(12) United States Patent
Petzoldt et al.

(10) Patent No.: US 7,777,082 B2
(45) Date of Patent: Aug. 17, 2010

(54) PREPARATION OF ANNULAR UNSUPPORTED CATALYSTS

(75) Inventors: Jochen Petzoldt, Weisenheim am Berg (DE); Klaus Joachim Mueller-Engel, Stutensee (DE); Signe Unverricht, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1258 days.

(21) Appl. No.: 10/934,525

(22) Filed: Sep. 7, 2004

(65) Prior Publication Data

US 2005/0065371 A1 Mar. 24, 2005

Related U.S. Application Data

(60) Provisional application No. 60/504,207, filed on Sep. 22, 2003.

(30) Foreign Application Priority Data

Sep. 22, 2003 (DE) ................. 103 44 149

(51) Int. Cl.
B01J 23/16 (2006.01)
B01J 23/18 (2006.01)
B01J 23/28 (2006.01)
B01J 23/31 (2006.01)
B01J 23/745 (2006.01)
C07C 45/27 (2006.01)

(52) U.S. Cl. ............ 568/469.9; 502/205; 502/212; 502/304; 502/306; 502/307; 502/308; 502/309; 502/310; 502/311; 502/312; 502/313; 502/314; 502/315; 502/316; 502/317; 502/321; 502/322; 568/470

(58) Field of Classification Search ............ 502/316, 502/300, 305, 306, 307, 308, 309, 310, 311, 502/313, 314, 321, 322, 323, 325, 328, 329, 502/330, 332, 336, 338, 503, 205, 212, 312, 502/315, 317, 304; 562/534; 568/449, 469.9, 568/470

See application file for complete search history.

(56) References Cited

U.S. PATENT DOCUMENTS 4,366,093 A 12/1982 Shiozaki et al.

(Continued)

FOREIGN PATENT DOCUMENTS

DE 33 00 044 7/1983

(Continued)

OTHER PUBLICATIONS

U.S. Appl. No. 10/974,831, filed Oct. 28, 2004, Petzoldt, et al.

(Continued)

*Primary Examiner*—Stanley Silverman
*Assistant Examiner*—Brittany M Martinez
(74) *Attorney, Agent, or Firm*—Oblon, Spivak, McClelland, Maier & Neustadt, L.L.P.

(57) ABSTRACT

A process for preparing annular unsupported catalysts by thermally treating annular shaped unsupported catalyst precursor bodies, wherein the side crushing strength of the annular shaped unsupported catalyst precursor bodies is $\geq 12$ N and $\leq 23$ N; such precursor bodies per se; annular unsupported catalysts having a specific pore structure; and a method of using such annular unsupported catalysts for the catalytic partial oxidative preparation in the gas phase of (meth)acrolein.

33 Claims, 18 Drawing Sheets

U.S. PATENT DOCUMENTS

| | | |
|---|---|---|
| 4,438,217 A | 3/1984 | Takata et al. |
| 4,892,856 A * | 1/1990 | Kawajiri et al. ............. 502/247 |
| 5,082,819 A | 1/1992 | Boeck et al. |
| 5,364,825 A | 11/1994 | Neumann et al. |
| 5,449,821 A | 9/1995 | Neumann et al. |
| 5,583,086 A | 12/1996 | Tenten et al. |
| 6,383,976 B1 | 5/2002 | Arnold et al. |
| 6,525,217 B1 | 2/2003 | Unverrict et al. |
| 6,740,779 B1 * | 5/2004 | Tenten et al. ................ 562/598 |
| 2001/0029235 A1 | 10/2001 | Walsdorff et al. |
| 2004/0034249 A1 | 2/2004 | Arnold et al. |
| 2004/0054222 A1 | 3/2004 | Felder et al. |
| 2004/0102648 A1 | 5/2004 | Borgmeier et al. |
| 2006/0074258 A1 | 4/2006 | Borgmeier et al. |

FOREIGN PATENT DOCUMENTS

| | | |
|---|---|---|
| DE | 33 38 380 A1 | 4/1984 |
| DE | 44 07 020 | 9/1994 |
| DE | 198 55 913 | 8/2000 |
| DE | 199 48 523 | 4/2001 |
| DE | 100 46 957 | 4/2002 |
| DE | 101 21 592 | 5/2002 |
| DE | 101 01 695 | 7/2002 |
| EP | 0 575 897 | 12/1993 |
| EP | 1 340 538 | 9/2003 |
| JP | 2001-293376 | 10/2001 |
| WO | 02/32571 | 4/2002 |
| WO | WO 02/062737 A2 | 8/2002 |

OTHER PUBLICATIONS

U.S. Appl. No. 11/107,919, filed Apr. 18, 2005, Cremer, et al.

* cited by examiner

PREPARATION OF ANNULAR UNSUPPORTED CATALYSTS

BACKGROUND OF THE INVENTION

Field of the Invention

The present invention relates to a process for preparing annular unsupported catalysts having a curved and/or uncurved top surface of the rings, whose active composition has a stoichiometry of the general formula I

$$Mo_{12}Bi_aFe_bX^1_cX^2_dX^3_eX^4_fO_n \qquad (I)$$

where
$X^1$=nickel and/or cobalt,
$X^2$=thallium, an alkali metal and/or an alkaline earth metal,
$X^3$=zinc, phosphorus, arsenic, boron, antimony, tin, -cerium, lead- and/or tungsten,
$X^4$=silicon, aluminum, titanium and/or zirconium,
a=from 0.2 to 5,
b=from 0.01 to 5,
c=from 0 to 10,
d=from 0 to 2,
e=from 0 to 8,
f=from 0 to 10 and
n=a number which is determined by the valenrv and frequency of the elements in I other than oxygen,
or a stoichiometry of the general formula II

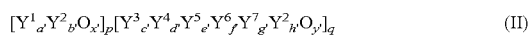

$$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \qquad (II)$$

where
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements vanadium, chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
a'=from 0.01 to 8,
b'=from 0.1 to 30,
c'=from 0 to 4,
d'=from 0 to 20,
e' is from >0 to 20,
f'=from 0 to 6,
g'=from 0 to 15,
h'=from 8 to 16,
x', y'=numbers which are determined by the valency and frequency of the elements in II other than oxygen and
p, q=numbers whose p/q ratio is from 0.1 to 10,
and whose annular geometry, without taking into account-any existing curvature of the top surface, has a length L of from 2 to 11 mm, an external diameter E of from 2 to 11 mm and a wall thickness W of from 0.75 mm to 1.75 mm,
by generating a finely divided shapeable mixture from sources of the elemental constituents of the active composition and, optionally after adding shaping and/or reinforcing assistants, forming from this mixture annular shaped unsupported catalyst precursor bodies whose top surfaces are curved and/or uncurved, and converting these to the annular unsupported catalysts by thermally treating at elevated temperature.

The present invention also relates to the use of the annular unsupported catalysts obtainable by the process according to the invention as catalysts having increased activity and selectivity for the catalytic partial oxidation in the gas phase of propene to acrolein and of isobutene or tert-butanol or its methyl ether to methacrolein.

DESCRIPTION OF THE BACKGROUND

Processes described at the outset for preparing annular unsupported catalysts are known (cf., for example, EP-A 575897, DE-A 3300044, DE-A 19855913, DE-A 10046957, EP-A 1340538, DE-A 19948523, DE-A 44070202 and DE-A 10101695). Likewise known from the aforementioned documents is the use of such annular unsupported catalysts as catalysts for the catalytic partial oxidation in the gas phase of propene to acrolein and of isobutene or tert-butanol or the methyl ether of tert-butanol to methacrolein.

With regard to the forces to be applied to shape the annular shaped unsupported catalyst precursor body, the prior art documents generally make no disclosure.

In this regard, only DE-A 10101695 and DE-A 10121592 teach that the compaction (compression) to the annular shaped unsupported catalyst precursor bodies should be effected in such a way that the side crushing strength of the resulting annular shaped unsupported catalyst precursor bodies is 10 N.

However, a disadvantage of, for example, the teaching of DE-A 10101695 is that when the annular unsupported catalysts resulting from the teaching of DE-A 10101695 are used as catalysts for the catalytic partial oxidation in the gas phase of propene to acrolein or of isobutene or tert-butanol (or its methyl ether) to methacrolein, they are not fully satisfactory either with regard to their activity or with regard to the selectivity of target product formation.

SUMMARY OF THE INVENTION

It is an object of the present invention to provide an improved process for preparing annular unsupported catalysts.

We have found that this object is achieved by a process as described at the outset, wherein the shaping (compression) to the annular shaped-unsupported catalyst precursor bodies is effected in such a way that the side crushing strength of the resulting annular shaped unsupported catalyst precursor bodies is $\geq 12$ N and $\leq 23$ N. The side crushing strength of the resulting annular shaped unsupported catalyst precursor bodies is preferably $\geq 13$ N and $\leq 22$ N or $\geq 14$ N and $\leq 21$ N. Very particular preference is given to the side crushing strength of the resulting annular shaped unsupported catalyst precursor bodies being $\geq 15$ N and $\leq 20$ N.

BRIEF DESCRIPTION OF THE DRAWINGS

The figures of the drawing show the pore distribution of various exemplified annular unsupported catalysts, both according to the invention and for purposes of comparison.

DETAILED DESCRIPTION OF THE INVENTION

Figure 1:
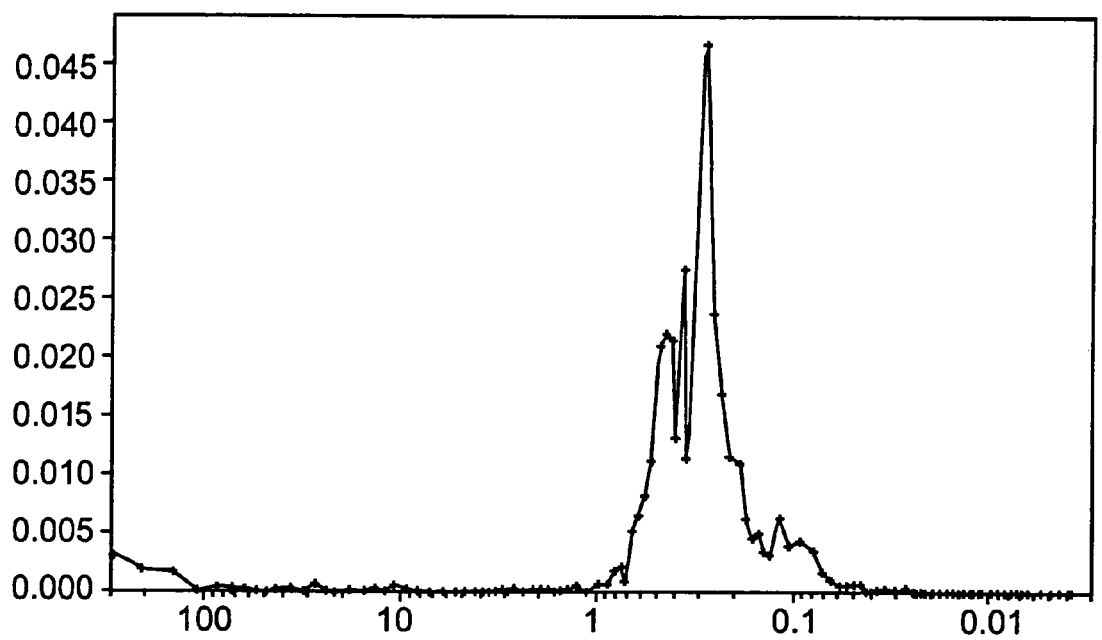
FIGS. 1 and 2 show the pore distribution of the annular unsupported catalyst EUC1.

According to the invention, the particle size of the finely divided shapeable mixture to be shaped to annular shaped unsupported catalyst precursor bodies is also advantageously from 200 μm to 1.5 mm, more advantageously from 400 μm to 1 mm. In a favorable manner, at least 80% by weight, better at least 90% by weight and more advantageously at least 95 or 98 or more % by weight, of the overall composition lies within this particle size range.

In this document, side crushing strength refers to the crushing strength when the annular shaped unsupported catalyst precursor body is compressed at right angles to the cylindrical shell (i.e. parallel to the surface of the ring orifice).

All side crushing strengths in this document relate to a determination by means of a material testing machine from Zwick GmbH & Co. (D-89079 Ulm) of the Z 2.5/TS1S type. This material testing machine is designed for quasistatic stress having a single-impetus, stationary, dynamic or varying profile. It is suitable for tensile, compressive and bending tests. The installed force transducer of the KAF-TC type from A.S.T. (D-01307 Dresden) having the manufacturer number 03-2038 was calibrated in accordance with DIN EN ISO 7500-1 and could be used for the 1-500 N measurement range (relative measurement uncertainty: ±0.2%).

The measurements were carried out with the following parameters:

Initial force: 0.5 N.

Rate of initial force: 10 mm/min.

Testing rate: 1.6 mm/min.

The upper die was initially lowered slowly down to just above the surface of the cylindrical shell of the annular shaped unsupported catalyst precursor body. The upper die was then stopped, in order subsequently to be lowered at the distinctly slower testing rate with the minimum initial force required for further lowering.

The initial force at which the shaped unsupported catalyst precursor body exhibits crack formation is the side crushing strength (SCS).

Unsupported catalyst ring geometries which are particularly advantageous in accordance with the invention additionally fulfill the condition L/E=from 0.3 to 0.7. Particular preference is given to L/E being from 0.4 to 0.6.

It is also advantageous in accordance with the invention when the I/E ratio (where I is the internal diameter of the unsupported catalyst ring geometry) is from 0.5 to 0.8, preferably from 0.6 to 0.7.

Particularly advantageous unsupported catalyst ring geometries are those which simultaneously have one of the advantageous L/E ratios and one of the advantageous I/E ratios. Such possible combinations are, for example, L/E=from 0.3 to 0.7 and I/E=from 0.5 to 0.8 or from 0.6 to 0.7. Alternatively, L/E may be from 0.4 to 0.6 and I/E simultaneously from 0.5 to 0.8 or from 0.6 to 0.7.

It is also preferred in accordance with the invention when L is from 2 to 6 mm and more preferred when L is from 2 to 4 mm.

It is also advantageous when E is from 4 to 8 mm, preferably from 5 to 7 mm.

The wall thickness of the unsupported catalyst ring geometries obtainable in accordance with the invention is advantageously from 1 to 1.5 mm.

In other words, unsupported catalyst ring geometries which are favorable in accordance with the invention are, for example, those where L=from 2 to 6 mm and E=from 4 to 8 mm or from 5 to 7 mm. Alternatively, L may be from 2 to 4 mm and E simultaneously from 4 to 8 mm or from 5 to 7 mm. In all the aforementioned cases, the wall thickness W may be from 0.75 to 1.75 mm or from 1 to 1.5 mm.

Among the aforementioned favorable unsupported catalyst geometries, particular preference is given to those for which the aforementioned L/E and I/E combinations are simultaneously fulfilled.

Possible unsupported catalyst ring geometries obtainable in accordance with the invention are thus (E×L×I) 5 mm×3 mm×2 mm, or 5 mm×3 mm×3 mm, or 5.5 mm×3 mm×3.5 mm, or 6 mm×3 mm×4 mm, or 6.5 mm×3 mm×4.5 mm, or 7 mm×3 mm×5 mm.

The top surfaces of the rings obtainable in accordance with the invention may also either both be, or only one may be, curved as described in EP-A 184790, and, for example, in such a way that the radius of the curvature is preferably from 0.4 to 5 times the external diameter A. Preference is given in accordance with the invention to both top surfaces being uncurved.

All of these unsupported catalyst ring geometries are suitable, for example, both for catalytic partial oxidation in the gas phase of propene to acrolein and for the catalytic partial oxidation in the gas phase of isobutene or tert-butanol or the methyl ether of tert-butanol to methacrolein.

Regarding the active compositions of the stoichiometry of the general formula I, the stoichiometric coefficient b is preferably from 2 to 4, the stoichiometric coefficient c is preferably from 3 to 10, the stoichiometric coefficient d is preferably from 0.02 to 2, the stoichiometric coefficient e is preferably from 0 to 5 and the stoichiometric coefficient a is preferably from 0.4 to 2. The stoichiometric coefficient f is advantageously from 0.5 or 1 to 10. Particular preference is given to the aforementioned stoichiometric coefficients simultaneously being within the preferred ranges mentioned.

In addition, $X^1$ is preferably cobalt, $X^2$ is preferably K, Cs and/or Sr, more preferably K, $X^3$ is preferably zinc and/or phosphorus and $X^4$ is preferably Si. Particular preference is given to the variables $X^1$ to $X^4$ simultaneously having the aforementioned definitions.

Particular preference is given to all stoichiometric coefficients a to f and all variables $X^1$ to $X^4$ simultaneously having their aforementioned advantageous definitions.

Within the stoichiometries of the general formula II, preference is given to those which correspond to the general formula III

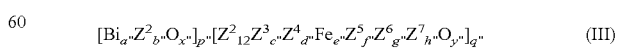  (III)

where $Z^2$=molybdenum or molybdenum and tungsten, $Z^3$=nickel and/or cobalt, preferably Ni, $Z^4$=thallium, an alkali metal and/or an alkaline earth metal, preferably K, Cs and/or Sr, $Z^5$=phosphorus, arsenic, boron, antimony, tin, cerium and/or Bi,
$Z^6$=silicon, aluminum, titanium and/or zirconium, preferably Si,
$Z^7$=copper, silver and/or gold,
a"=from 0.1 to 1,
b"=from 0.2 to 2,
c"=from 3 to 10,
d"=from 0.02 to 2,
e"=from 0.01 to 5, preferably 0.1 to 3,
f"=from 0 to 5,
g"=from 0 to 10, preferably from >0 to 10, more preferably from 0.2 to 10 and most preferably from 0.4 to 3,
h"=from 0 to 1,
x", y"=numbers which are determined by the valency and frequency of the elements in III other than oxygen and
p", q"=numbers whose p"/q" ratio is from 0.1 to 5, preferably from 0.5 to 2.

In addition, preference is given in accordance with the invention to active compositions of the stoichiometry 11 which contain three-dimensional regions of the chemical composition $Y^1{}_{a'}Y^2{}_{b'}O_{x'}$ which are delimited from their local environment as a consequence of their different composition from their local environment and whose longest diameter (longest line passing through the center of the region and connecting two points on the surface (interface) of the region) is from 1 nm to 100 μm, frequently from 10 nm to 500 nm or from 1 μm to 50 or 25 μm.

Active compositions of the stoichiometry II obtainable particularly advantageously in accordance with the invention are those in which $Y^1$ is only bismuth.

Within the active compositions of the stoichiometry III, preference is given in accordance with the invention to those in which $Z^2{}_{b''}$=(tungsten)$_{b''}$ and $Z^2{}_{12}$=(molybdenum)$_{12}$.

In addition, preference is given in accordance with the invention to active compositions of the stoichiometry III which contain three-dimensional regions of the chemical composition $Bi_{a''}Z^2{}_{b''}O_{x''}$ which are delimited from their local environment as a consequence of their different composition from their local environment and whose longest diameter (longest line passing through the center of the region and connecting two points on the surface (interface) of the region) is from 1 nm to 100 μm, frequently from 10 nm to 500 nm or from 1 μm to 50 or 25 μm.

In addition, it is advantageous when at least 25 mol %, (preferably at least 50 mol % and more preferably at least 100 mol %) of the total $[Y^1{}_{a'}Y^2{}_{b'}O_{x'}]_p([Bi_{a''}Z^2{}_{b''}O_{x''}]_{p''})$ fraction of the active compositions of the stoichiometry II (active compositions of the stoichiometry III) obtainable in accordance with the invention in the active compositions of the stoichiometry II (active compositions of the stoichiometry III)) is in the form of three-dimensional regions of the chemical composition $Y^1{}_{a'}Y^2{}_{b'}O_{d'}([Bi_{a''}Z^2{}_{b''}O_{x''}])$ which are delimited from their local environment as a consequence of their different chemical composition to their local environment and whose longest diameter is in the range from 1 nm to 100 μm.

Useful shaping assistants (lubricants) for the process according to the invention are, for example, carbon black, stearic acid, starch, polyacrylic acid, mineral or vegetable oil, water, boron trifluoride or graphite. Glycerol and cellulose ether may also be used as lubricants. Based on the composition to be shaped to the shaped unsupported catalyst precursor body, generally ≦5% by weight, usually ≦3% by weight, in many cases ≦2% by weight, of shaping assistant is used. Typically, the aforementioned addition amount is ≧0.5% by weight. The preferred lubricating assistant in accordance with the invention is graphite.

In the course of the thermal treatment of the annular shaped unsupported catalyst precursor bodies, the shaping assistants are usually substantially decomposed to gaseous components and/or combusted, so that the annular unsupported catalyst obtainable in accordance with the invention is normally partly or completely free of shaping assistants used. When shaping assistant is present in the annular unsupported catalysts obtainable in accordance with the invention, it behaves substantially inertly with respect to the partial oxidations catalyzed by the unsupported catalysts.

The latter is also true of any finely divided reinforcing agents added before the shaping, such as microfibers of glass, asbestos, silicon carbide or potassium titanate. The shaping to the annular shaped unsupported catalyst precursor body may be carried out, for example, by means of a tableting machine, an extrusion reshaping machine or the like.

The annular shaped unsupported catalyst precursor body is thermally treated generally at temperatures which exceed 350° C. Normally, the temperature in the course of the thermal treatment will not exceed 650° C. Advantageously in accordance with the invention, the temperature in the course of the thermal treatment will not exceed 600° C., preferably 550° C. and more preferably 500° C. In addition, the temperature in the course of the thermal treatment of the annular shaped unsupported catalyst precursor body in the process according to the invention will preferably exceed 380° C., advantageously 400° C., particularly advantageously 420° C. and most preferably 440° C. The thermal treatment may also be subdivided into a plurality of sections within its duration. For example, a thermal treatment may initially be carried out at a temperature of from 150 to 350° C., preferably from 220 to 280° C., and be followed by a thermal treatment at a temperature of from 400 to 600° C., preferably from 430 to 550° C.

Normally, the thermal treatment of the annular shaped unsupported catalyst precursor body takes several hours (usually more than 5 h). Frequently, the overall duration of the thermal treatment extends for more than 10 h. Usually, treatment durations of 45 h or 25 h are not exceeded in the course of the thermal treatment of the annular shaped unsupported catalyst precursor body. Often, the overall treatment time is below 20 h. Advantageously in accordance with the invention, 500° C. (460° C.) are not exceeded in the course of the thermal treatment according to the invention of the annular shaped unsupported catalyst precursor body, and the treatment time within the temperature window of ≧400° C. (≧440° C.) extends to from 5 to 20 h.

The thermal treatment (and also the decomposition phase addressed hereinbelow) of the annular shaped unsupported catalyst precursor bodies may be effected either under inert gas or under an oxidative atmosphere, for example air (mixture of inert gas and oxygen) or else under a reducing atmosphere (for example mixture of inert gas, $NH_3$, CO and/or $H_2$ or methane, acrolein, methacrolein). It will be appreciated that the thermal treatment may also be performed under reduced pressure.

In principle, the thermal treatment of the annular shaped unsupported catalyst precursor bodies may be carried out in highly differing furnace types, for example heatable forced-air chambers, tray furnaces, rotary tube furnaces, belt calciners or shaft furnaces. Preference is given in accordance with the invention to effecting the thermal treatment of the annular shaped unsupported catalyst precursor bodies in a belt calcining apparatus as recommended by DE-A 10046957 and WO 02/24620.

The thermal treatment of the annular shaped unsupported catalyst precursor bodies below 350° C. generally follows the thermal treatment of the sources of the elemental constituents of the desired annular unsupported catalyst present in the shaped unsupported catalyst precursor bodies. Frequently, this decomposition phase in the process according to the invention proceeds in the course of the heating at temperatures of $\geqq 350°$ C.

The annular shaped unsupported catalyst precursor bodies of annular unsupported catalysts obtainable in accordance with the invention, whose active composition has a stoichiometry of the general formula I, or the general formula II, or the general formula III, may be prepared in the inventive manner by generating, from sources of the elemental constituents of the active composition of the desired annular unsupported catalyst, a (very intimate) finely divided shapeable mixture having a composition corresponding to the stoichiometry of the desired active composition and, optionally after adding shaping and/or reinforcing assistants, forming from this an annular unsupported shaped catalyst precursor body (having curved and/or uncurved top surfaces) whose side crushing strength is $\geqq 12$ N and $\leqq 23$ N. The geometry of the annular shaped unsupported catalyst precursor body will correspond substantially to that of the desired annular unsupported catalyst.

Useful sources for the elemental constituents of the desired active composition are those compounds which are already oxides and/or those compounds which can be converted to oxides by heating, at least in the absence of oxygen.

In addition to the oxides, useful such starting compounds are in particular halides, nitrates, formates, oxalates, citrates, acetates, carbonates, amine complexes, ammonium salts and/ or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or may be decomposed in the course of later calcining at the latest to give compounds which escape fully in gaseous form may additionally be incorporated into the finely divided shapeable mixture (preferably a dry mixture)).

The preferably intimate mixing of the starting compounds (sources) to prepare the finely divided shapeable mixture in the process according to the invention may be effected in dry or in wet form. When it is effected in dry form, the starting compounds are appropriately used as a finely divided powder (the particle size should advantageously be $\leqq 100$ μm, preferably $\leqq 50$ μm; in general the number-average largest particle diameter will be $\geqq 10$ μm). After any addition of shaping and/or reinforcing assistants, the shaping to the annular shaped unsupported catalyst precursor body may subsequently be effected.

However, preference is given in accordance with the invention to effecting the intimate mixing in wet form. Typically, the starting compounds are mixed together in the form of an aqueous solution and/or suspension. Particularly intimate shapeable mixtures are obtained when the starting materials are exclusively sources of the elemental constituents present in dissolved form. The solvent used is preferably water. Subsequently, the resulting solution or suspension is dried, and the drying process is preferably effected by spray drying with exit temperatures of from 100 to 150° C. The particle size of the resulting spray powder is typically from 20 to 50 μm.

The spray powder may then be compressed (shaped) as such or after addition of shaping and/or reinforcing assistants to give the annular shaped unsupported catalyst precursor bodies. However, the finely divided reinforcing assistants may also be (partly or fully) added in advance of the spray drying. It is also possible in the course of the drying to only partly remove the solvent or suspension agent if the intention is to use it as a shaping assistant.

Instead of shaping the spray powder, optionally after adding shaping and/or reinforcing assistants, directly to the annular shaped unsupported catalyst precursor bodies (having curved and/or uncurved top surface of the rings), it is frequently appropriate to initially carry out an intermediate compaction in order to coarsen the powder (generally to a particle size of from 400 μm to 1 mm). Subsequently, the actual ring shaping is effected with the coarsened powder, and finely divided lubricant may again be added beforehand if required.

A favorable lubricant for such an intermediate compaction (and likewise for the final shaping) has been found to be finely divided graphite from Timcal AG (San Antonio, US) of the TIMREX P44 type, or T44 graphite powder from Lonza, CH-5643 Sins (sieve analysis or laser diffraction: min. 50% by weight <24 μm, max. 10% by weight >24 μm and <48 μm, max. 5% by weight >48 μm, BET surface area: from 6 to 13 $m^2/g$). After the completed intermediate compaction, it functions simultaneously as a lubricant in the actual ring shaping (and may, if required, additionally be supplemented as described above). It is found to be favorable when the ash residue of the graphite used (calcining at 815° C. under air) is $\leqq 0.1\%$ by weight.

Such an intermediate compaction for the purpose of particle coarsening may be effected, for example, by means of a compactor from Hosokawa Bepex GmbH (D-74211 Leingarten), of the K 200/100 compactor type. The hardness of the intermediate compactate is frequently already in the region of 10 N. Useful for the ring shaping to the shaped unsupported catalyst precursor body is, for example, a Kilian rotary tableting press (from Kilian in D-50735 Cologne) of the RX 73 or S 100 type. Alternatively, a tableting press from Korsch (D-13509 Berlin) of the PH 800-65 type may be used.

Especially for preparing active compositions of the stoichiometry of the general formula II or III, it is advantageous to preform a mixed oxide $Y^1{}_a\cdot Y^2{}_b\cdot O_{x'}$ or $Bi_{a''}Z^2{}_{b''}O_{x''}$ as the source of the elements $Y^1$, $Y^2$ and Bi, $Z^2$ respectively in the absence of the remaining constituents of the active compositions of the stoichiometry of the general formula II or III and thus, after its preformation, as already described, to generate a finely divided shapeable mixture using sources of the remaining constituents of the active compositions of the stoichiometry of the general formula II or III, in order to shape therefrom, optionally after adding shaping and/or reinforcing assistants, the annular shaped unsupported catalyst precursor bodies.

In such a procedure, care has to be taken merely that, in the case that the preparation of the finely divided shapeable mixture is effected in wet form (in suspension), the preformed mixed oxides $Y^1{}_a\cdot Y^2{}_b\cdot O_{x'}$ or $Bi_{a''}Z^2{}_{b''}O_{x''}$ do not go into solution to a significant extent.

A preparation method as described above is described in detail in the documents DE-A 4407020, EP-A 835, EP-A 575897 and DE-C 3338380.

For example, water-soluble salts of $Y^1$ such as nitrates, carbonates, hydroxides or acetates may be mixed in water with $Y^2$ acids or their ammonium salts, the mixture dried (preferably spray-dried) and the dried composition subsequently thermally treated. The thermally treated composition is subsequently appropriately comminuted (for example in a ball mill or by jet milling) and, from the powder which generally consists of substantially spherical particles and is obtainable in this way, the particle class having a largest particle diameter lying within the desired largest diameter range desired for the active composition of the stoichiometry of the general formula II or III is separated by classification to be carried out in a manner known per se (for example wet or dry sieving) and is preferably mixed with, based on the mass of this separated particle class, from 0.1 to 3% by weight of finely divided $SiO_2$ (the number-average largest particle diameter of the typically substantially spherical $SiO_2$ particles is appropriately from 10 to 50 nm), thus producing a starting composition 1. The thermal treatment is appropriately effected at temperatures of from 400 to 900° C., preferably from 600 to 900° C. The latter is especially true when the preformed mixed oxide is one of the stoichiometry $Bi_2Z^2O_6$, $Bi_2Z^2{}_2O_9$ and/or $Bi_2Z^2{}_3O_{12}$, among which $Bi_2Z^2{}_2O_9$ is preferred, especially when $Z^2$=tungsten.

Typically the thermal treatment is effected in an airstream (for example in a rotary tube furnace as described in DE-A 10325487). The duration of the thermal treatment generally extends to a few hours.

The remaining constituents of the desired active composition of the general formula II or III are normally used to prepare, starting from sources which are suitable in a manner known per se (cf EP-A 835 and DE-C 3338380 and also DE-A 4407020), in an inventively appropriate manner, for example, a very intimate, preferably finely divided dry mixture (for example combining water-soluble salts such as halides, nitrates, acetates, carbonates of hydroxides in an aqueous solution and subsequently, for example, spray-drying the aqueous solution, or suspending water-insoluble salts, for example oxides, in aqueous medium and subsequently, for example, spray-drying the suspension) which is referred to here as starting composition 2. It is essential only that the constituents of the starting composition 2 are either already oxides or compounds which can be converted to oxides by heating, in the absence or presence of oxygen. Subsequently, the starting composition 1 and the starting composition 2 are mixed in the desired ratio in the inventive manner, optionally after adding shaping and/or reinforcing assistants, to give the mixture which can be shaped to the annular shaped unsupported catalyst precursor body. The shaping may, as already described, appropriately from an application point of view, be effected by an intermediate compaction stage.

In a less preferred embodiment, the preformed mixed oxide $Y^1{}_{a'}Y^2{}_{b'}O_{x'}$ or $Bi_{a''}Z^2{}_{b''}O_{x''}$ may also be intimately mixed with sources of the remaining constituents of the desired active composition in liquid, preferably aqueous, medium. This mixture is subsequently, for example, dried to give an intimate dry mixture and then, as already described, shaped and thermally treated. The sources of the remaining constituents may be dissolved and/or suspended in this liquid medium, whereas the preformed mixed oxide should be substantially insoluble, i.e. has to be suspended, in this liquid medium.

The preformed mixed oxide particles are present having a substantially unchanged longitudinal dimension established by the classification in the finished annular unsupported catalyst.

Preference is given in accordance with the invention to the specific surface area of mixed oxides $Y^1{}_{a'}Y^2{}_{b'}O_{x'}$ or $Bi_{a''}Z^2{}_{b''}O_{x''}$ preformed in this way being from 0.2 to 2 m$^2$/g, preferably from 0.5 to 1.2 m$^2$/g. In addition, the total pore volume of mixed oxides preformed in this way advantageously results predominantly from micropores.

All data in this document on determinations of specific surface areas or on micropore volumes relates to the determinations to DIN 66131 (determination of the specific surface area of solids by gas adsorption ($N_2$) according to Brunauer-Emmet-Teller (BET)).

All data in this document on determinations of total pore volumes and also of diameter-distributions on these total pore volumes relate, unless stated otherwise, to determinations by the mercury porosimetry method employing the Auto Pore 9220 instrument from Micromeritics GmbH, 4040 Neuss, DE (bandwidth from 30 Å to 0.3 mm).

Annular unsupported catalysts obtained advantageously in accordance with the invention are those whose specific surface area S is from 5 to 20 or 15 m$^2$/g, frequently from 5 to 10 m$^2$/g. According to the invention, the total pore volume of the annular unsupported catalysts obtained in accordance with the invention is advantageously in the range from 0.1 to 1 or 0.8 cm$^3$/g, frequently in the range from 0.2 to 0.4 cm$^3$/g.

In contrast to the teaching of WO 03/039744 and to the teaching of EP-A 279374, the different pore diameters in annular unsupported catalysts obtained in accordance with the invention advantageously contribute to the total pore volume as follows:

pores having a diameter in the range from <0.03 µm: ≦5% by volume;

pores having a diameter in the range from ≧0.03 to ≦0.1 µm: <25% by volume;

pores having a diameter in the range from >0.1 to ≦1 µm: ≧70% by volume and pores having a diameter in the range from ≧1 to ≦10 µm: ≦10% by volume.

In other words, in contrast to the teaching of EP-A 279374, the proportion of the pores having a diameter of ≧1 µm generally plays only a minor role in annular unsupported catalysts obtained in accordance with the invention.

In addition, the proportion of pores having a diameter in the range from ≧0.03 to ≦0.1 µm in annular unsupported catalysts obtained in accordance with the invention generally plays a relatively minor role.

Particularly advantageously, the proportion of the different pore diameters in the total pore volume in annular unsupported catalysts obtained in accordance with the invention has the following distribution:

pores having a diameter in the range from <0.03 µm: ≧0 and ≦5% by volume, preferably ≦3% by volume, pores having a diameter in the range from ≦0.03 to ≦0.1 µm: >3 or ≧5 and ≦20 or ≦15% by volume;

pores having a diameter in the range from >0.1 to <1 µm: ≧75 or ≧80 and ≦95 or ≦90% by volume;

pores having a diameter in the range from >1 µm to ≦10 µm: ≧0 and ≦5% by volume, preferably ≦3% by volume.

In other words, for annular unsupported catalysts obtained advantageously in accordance with the invention, the pore diameter range from >0.1 to <1 µm plays the decisive role with regard to their performance when they are used as catalysts for the partial oxidation of propene to acrolein, or isobutene or tert-butanol or the methyl ether of tert-butanol to methacrolein.

In contrast, pores in the pore diameter range from 0.01 to 0.1 µm promote the partial oxidation of propene to acrylic acid. This is advantageous when the active composition is used in the first stage of a two-stage partial oxidation of propene to acrylic acid, since acrylic acid formed in the first stage is substantially preserved in the second stage.

The aforementioned is also additionally confirmed by inventively obtained, particularly advantageous annular unsupported catalysts not only fulfilling the aforementioned conditions with regard to specific surface area S, total pore volume V and pore diameter distribution, but also additionally the pore diameter $d^{max}$ making the largest percentage contribution to the total pore volume V lying within the diameter range from 0.3 to 0.8 µm, particularly advantageously in the diameter range from 0.4 to 0.7 μm and very particularly advantageously in the diameter range from 0.5 to 0.6 μm.

A surprising feature of the invention is that with increasing side crushing strength of the annular shaped unsupported catalyst precursor body, the pore diameter in the resulting unsupported catalyst range is generally shifted to larger values.

This is surprising in that the side crushing strength of the resulting annular unsupported catalyst is simultaneously shifted to higher values. Surprisingly, the side crushing strength of the annular unsupported catalyst resulting in accordance with the invention is generally less than the side crushing strength of the corresponding annular shaped unsupported catalyst precursor body.

Typically, the side crushing strengths of annular unsupported catalysts obtainable in accordance with the invention are from 5 to 13 N, frequently from 8 to 11 N. These side crushing strengths of annular unsupported catalysts obtainable in accordance with the invention are normally also present when the remaining physical properties described as advantageous (for example S, V and pore diameter distribution) of annular unsupported catalysts obtainable by the process according to the invention are present.

As already mentioned, the annular unsupported catalysts obtainable in accordance with the invention are especially suitable as catalysts for the partial oxidation of propene to acrolein or of isobutene and/or tert-butanol to methacrolein. The partial oxidation may be carried out as described, for example, in the documents WO 00/53557, WO 00/53558, DE-A 199 10 506, EP-A1 106 598, WO 01/36364, DE-A 199 27 624, DE-A 199 48 248, DE-A 199 48 523, DE-A 199 48 241, EP-A 700 714, DE-A 10313213, DE-A 10313209, DE-A 10232748, DE-A 10313208, WO 03/039744. EP-A 279 374, DE-A 33 38 380, DE-A 33 00 044, EP-A 575 897 and DE-A 44 07 020, and the catalyst charge may comprise, for example, only annular unsupported catalysts obtainable by the process according to the invention or, for example, annular unsupported catalysts diluted with inert shaped bodies. In the latter case, the catalyst charge, advantageously in accordance with the invention, is generally configured in such a way that its volume-specific activity increases continuously, sharply and/or in stages in the flow direction of the reaction gas mixture.

The ring geometries of the unsupported catalysts obtainable in accordance with the invention emphasized individually in this document are found to be especially advantageous when the hourly space velocity on the catalyst charge of propene, isobutene and/or tert-butanol (or its methyl ether) present in the starting reaction gas mixture is $\geq 130$ l (STP)/l of catalyst charge·h (upstream and/or downstream beds of pure inert material are not regarded as belonging to the catalyst charge in hourly space velocity considerations). This is especially true when the other physical properties, described as advantageous in this document, of annular unsupported catalysts obtainable in accordance with the invention are also present.

However, this advantageous behavior of annular unsupported catalysts obtainable in accordance with the invention, in particular the aforementioned, is also present when the aforementioned hourly space velocity on the catalyst charge is $\geq 140$ l(STP)/l·h, or $\geq 150$ l (STP)/l·h, or $\geq 160$ l (STP)/l·h. Normally, the aforementioned hourly space velocity on the catalyst charge will be $\leq 600$ l (STP)/l·h, frequently $\leq 500$ l (STP)/l·h, in many cases $\leq 400$ l (STP)/l·h or $\leq 350$ l (STP)/l·h. Hourly space velocities in the range from 160 l (STP)/l·h to 300 or 250 or 200 l (STP)/l·h are particularly typical.

It will be appreciated that the annular unsupported catalysts obtainable in accordance with the invention may also be used as catalysts for the partial oxidation of propene to acrolein or of isobutene and/or tert-butanol (or its methyl ether) to methacrolein at hourly space velocities on the catalyst charge of the starting compound to be partially oxidized of $<130$ l (STP)/l·h, or $\leq 120$ l (STP)/l·h, or $<110$ l (STP)/l·h. However, this hourly space velocity will generally be at values of $\geq 60$ l (STP)/l·h, or $\geq 70$ l (STP)/l·h, or $\geq 80$ l (STP)/l·h.

In principle, the hourly space velocity on the catalyst charge of the starting compound to be partially oxidized (propene, isobutene and/or tert-butanol (or its methyl ether)) may be adjusted using two adjusting screws:

a) the hourly space velocity on the catalyst charge of starting reaction gas mixture; and/or b) the content in the starting reaction gas mixture of the starting compound to be partially oxidized.

The annular unsupported catalysts obtainable in accordance with the invention are also especially suitable when, at hourly space velocities on the catalyst charge of the organic compound to be partially oxidized which are above 130 l(STP)/l·h, the hourly space velocity is adjusted in particular using the aforementioned adjusting screw a).

The propene fraction (isobutene fraction or tert-butanol fraction (or its methyl ether fraction)) in the starting reaction gas mixture will generally be (i.e. essentially irrespective of the hourly space velocity) from 4 to 20% by volume, frequently from 5 to 15% by volume, or from 5 to 12% by volume, or from 5 to 8% by volume (based in each case on the total volume).

Frequently, the process of the partial oxidation catalyzed by the annular unsupported catalysts obtainable in accordance with the invention will be carried out (essentially irrespective of the hourly space velocity) at an (organic) compound to be partially oxidized (e.g. propene):oxygen:inert gases (including steam) volume ratio in the starting reaction gas mixture of from 1:(1.0 to 3.0):(5 to 25), preferably 1:(1.5 to 2.3):(10 to 15).

Inert gases refer to those gases of which at least 95 mol %, preferably at least 98 mol %, remains chemically unchanged in the course of the partial oxidation.

In the above-described starting reaction gas mixtures, the inert gas may consist of $\geq 20\%$ by volume, or $\geq 30\%$ by volume, or $\geq 40\%$ by volume, or $\geq 50\%$ by volume, or $\geq 60\%$ by volume, or $\geq 70\%$ by volume or $\geq 80\%$ by volume, or $\geq 90\%$ by volume or $\geq 95\%$ by volume, of molecular nitrogen.

However, when the hourly space velocities on the catalyst charge of the organic compound to be partially oxidized are $\geq 250$ l(STP)/l·h, it is recommended to use inert diluent gases such as propane, ethane, methane, pentane, butane, $CO_2$, CO, steam and/or noble gases for the starting reaction gas mixture. Generally, these inert gases and their mixtures may also be used even at lower inventive hourly space velocities on the catalyst charge of the organic compound to be partially oxidized. Cycle gas may also be used as a diluent gas. Cycle gas refers to the residual gas which remains when the target compound is substantially selectively removed from the product gas mixture of the partial oxidation. It has to be taken into account that the partial oxidations to acrolein or methacrolein using the annular unsupported catalysts obtainable in accordance with the invention may only be the first stage of a two-stage partial oxidation to acrylic acid or methacrylic acid as the actual target compounds, so that the cycle gas is then not usually formed until after the second stage. In such a two-stage partial oxidation, the product gas mixture of the first stage is generally fed as such, optionally after cooling and/or secondary oxygen addition, to the second partial oxidation stage.

In the partial oxidation of propene to acrolein using the annular unsupported catalysts obtainable in accordance with the invention, a typical composition of the starting reaction gas mixture (irrespective of the hourly space velocity selected) may comprise, for example, the following components:

from 6 to 6.5% by volume of propene,
from 3 to 3.5% by volume of $H_2O$,
from 0.3 to 0.5% by volume of CO,
from 0.8 to 1.2% by volume of $CO_2$,
from 0.025 to 0.04% by volume of acrolein,
from 10.4 to 10.7% by volume of $O_2$ and
as the remainder ad 100%, molecular oxygen, or:
5.4% by volume of propene,
10.5% by volume of oxygen,
1.2% by volume of $CO_x$,
81.3% by volume of $N_2$ and
1.6% by volume of $H_2O$.

However, the starting reaction gas mixture may also have the following composition:

from 6 to 15% by volume of propene,
from 4 to 30% by volume (frequently from 6 to 15% by volume) of water,
from $\geq 0$ to 10% by volume (preferably from $\geq 0$ to 5% by volume) of constituents other than propene, water, oxygen and nitrogen, and sufficient molecular oxygen that the molar ratio of molecular oxygen present to molecular propene present is from 1.5 to 2.5, and, as the remainder up to 100% by volume of the total amount, molecular nitrogen.

Another possible starting reaction gas mixture composition may comprise:

6.0% by volume of propene,
60% by volume of air and
34% by volume of $H_2O$.

Alternatively, starting reaction gas mixtures of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used.

The annular catalysts obtainable in accordance with the invention are also suitable for the processes of DE-A 10246119 and DE-A 10245585.

Further starting reaction gas mixtures which are suitable in accordance with the invention may lie within the following composition framework:

from 7 to 11% by volume of propene,
from 6 to 12% by volume of water,
from $\geq 0$ to 5% by volume of constituents other than propene, water, oxygen and nitrogen
sufficient molecular oxygen that the molar ratio of oxygen present to molecular propene present is from 1.6 to 2.2, and
as the remainder up to 100% by volume of the total amount, molecular nitrogen.

In the case of methacrolein as the target compound, the starting reaction gas mixture may in particular have the composition described in DE-A 44 07 020.

The reaction temperature for the propene partial oxidation when the annular unsupported catalysts obtainable in accordance with the invention are used is frequently from 300 to 380° C. The same also applies in the case of methacrolein as the target compound.

The reaction pressure for the aforementioned partial oxidations is generally from 0.5 or 1.5 to 3 or 4 bar.

The total hourly space velocity on the catalyst charge of starting reaction gas mixture in the aforementioned partial oxidations typically amounts to from 1000 to 10000 l(STP)/l·h, usually to from 1500 to 5000 l(STP)/l·h and often to from 2000 to 4000 l(STP)/l·h.

The propene to be used in the starting reaction gas mixture is in particular polymer-grade propene and chemical-grade propene, as described, for example, in DE-A 10232748.

The oxygen source used is normally air.

In the simplest case, the partial oxidation employing the annular unsupported catalysts obtainable in accordance with the invention may be carried out, for example, in a one-zone multiple catalyst tube fixed bed reactor, as described by DE-A 44 31 957, EP-A 700 714 and EP-A 700 893.

Customarily, the catalyst tubes in the aforementioned tube bundle reactors are manufactured from ferritic steel and typically have a wall thickness of from 1 to 3 mm. Their internal diameter is generally from 20 to 30 mm, frequently from 22 to 26 mm. A typical catalyst tube length is, for example, 3.20 m. It is appropriate from an application point of view for the number of catalyst tubes accommodated in the tube bundle vessel to be at least 5000, preferably at least 1000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf. EP-B 468 290).

However, the partial oxidation may also be carried out in a multizone (for example two-zone) multiple catalyst tube fixed bed reactor, as recommended by DE-A 199 10 506, DE-A 10313213, DE-A 10313208 and EP-A 1 106 598, especially at elevated hourly space velocities on the catalyst charge of the organic compound to be partially oxidized. A typical catalyst tube length in the case of a two-zone multiple catalyst tube fixed bed reactor is 3.50 m. Everything else is substantially as described for the one-zone multiple catalyst tube fixed bed reactor. Around the catalyst tubes, within which the catalyst charge is disposed, a heat exchange medium is conducted in each heating zone. Useful such media are, for example, melts of salts such as potassium nitrate, potassium nitrite, sodium nitrite and/or sodium nitrate, or of low-melting metals such as sodium, mercury and also alloys of different metals. The flow rate of the heat exchange medium within the particular heating zone is generally selected in such a way that the temperature of the heat exchange medium rises from the entry point into the temperature zone to the exit point from the temperature zone by from 0 to 15° C., frequently from 1 to 10° C., or from 2 to 8° C., or from 3 to 6° C.

The entrance temperature of the heat exchange medium which, viewed over the particular heating zone, may be conducted in cocurrent or in countercurrent to the reaction gas mixture is preferably selected as recommended in the documents EP-A 1 106 598, DE-A 19948523, DE-A 19948248, DE-A 10313209, EP-A 700 714, DE-A 10313208, DE-A 10313213, WO 00/53557, WO 00/53558, WO 01/36364, WO 00/53557 and also the other documents cited as prior art in this document. Within the heating zone, the heat exchange medium is preferably conducted in a meandering manner. In general, the multiple catalyst tube fixed bed reactor additionally has thermal tubes for determining the gas temperature in the catalyst bed. Appropriately, the internal diameter of the thermal tubes and the diameter of the internal accommodating sleeve for the thermal element are selected in such a way that the ratio of volume developing heat of reaction to surface area removing heat for the thermal tube and working tubes is the same.

The pressure drop in the case of working tubes and thermal tube, based on the same GHSV, should be the same. The pressure drop may be equalized in the case of the thermal tube by adding spalled catalyst to the shaped catalyst bodies. This equalization is appropriately effected homogeneously over the entire thermal tube length.

To prepare the catalyst charge in the catalyst tubes in the process according to the invention, as already mentioned, it is possible only to use annular unsupported catalysts obtainable in accordance with the invention or, for example also substantially homogeneous mixtures of annular unsupported catalysts obtainable in accordance with the invention and shaped bodies which have no active composition and behave substantially inertly with respect to the heterogeneously catalyzed partial gas phase oxidation. Useful materials for such inert shaped bodies include, for example, porous or nonporous aluminum oxides, silicon dioxide, thorium dioxide, zirconium dioxide, silicon carbide, silicates such as magnesium or aluminum silicate or steatite (for example of the C220 type from CeramTec, Germany).

The geometry of such inert shaped diluent bodies may in principle be as desired. In other words, they may be, for example, spheres, polygons, solid cylinders or else, like the shaped catalyst bodies, rings. Frequently, the inert shaped diluent bodies selected will be those whose geometry corresponds to that of the shaped catalyst bodies to be diluted with them. However, along the catalyst charge, the geometry of the shaped catalyst body may also be changed or shaped catalyst bodies of different geometry may be used in a substantially homogeneous mixture. In a less preferred procedure, the active composition of the shaped catalyst body may also be changed along the catalyst charge.

Quite generally, as already mentioned, the catalyst charge is advantageously configured in such a way that the volume-specific (i.e. normalized to the unit of the volume) activity either remains constant or increases (continuously, sharply or stepwise) in the flow direction of the reaction gas mixture).

A reduction in the volume-specific activity may be achieved in a simple manner, for example, by homogeneously diluting a basic amount of annular unsupported catalysts prepared uniformly in accordance with the invention with inert shaped diluent bodies. The higher the proportion of the shaped diluent bodies is selected, the lower the active composition, i.e. catalyst activity, present in a certain volume of the charge. However, a reduction can also be achieved by changing the geometry of the annular unsupported catalysts obtainable in accordance with the invention in such a way that the amount of active composition present in the unit of the total ring volume (including the ring orifice) becomes smaller.

For the heterogeneously catalyzed gas phase partial oxidations using the annular unsupported catalysts obtainable in accordance with the invention, the catalyst charge is preferably either configured uniformly with only one unsupported catalyst ring over the entire length or structured as follows. Initially to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), in each case of the total length of the catalyst charge, a substantially homogeneous mixture of annular unsupported catalyst obtainable in accordance with the invention and inert shaped diluent bodies (both preferably having substantially the same geometry), the proportion by weight of the shaped diluent bodies (the mass densities of shaped catalyst bodies and of shaped diluent bodies generally differ only slightly) being normally from 5 to 40% by weight, or from 10 to 40% by weight, or from 20 to 40% by weight, or from 25 to 35% by weight. Downstream of this first charge section, there is then advantageously, up to the end of the length of the catalyst charge (i.e., for example, to a length of from 2.00 to 3.00 m, preferably from 2.50 to 3.00 m), either a bed of the annular unsupported catalyst obtainable in accordance with the invention which is diluted only to a lesser extent (than in the first section), or, most preferably, an unaccompanied (undiluted) bed of the same annular unsupported catalyst which has also been used in the first section. Of course, a constant dilution may also be selected over the entire charge. Charging may also be effected in the first section using only an annular unsupported catalyst obtainable in accordance with the invention and having lower active composition density based on its space demands, and, in the second section, using an annular unsupported catalyst obtainable in accordance with the invention having higher active composition density based on its space demands (for example 6.5 mm×3 mm×4.5 mm [E×L×1] in the first section, and 5×2×2 mm in the second section).

Overall, in a partial oxidation for preparing acrolein or methacrolein carried out using the annular unsupported catalysts obtainable in accordance with the invention, the catalyst charge, the starting reaction gas mixture, the hourly space velocity and the reaction temperature are generally selected in such a way that, on single pass of the reaction gas mixture through the catalyst charge, a conversion of the organic compound to be partially oxidized (propene, isobutane, tert-butanol or its methyl ether group) of at least 90 mol %, or 92 mol %, preferably of at least 95 mol %, results. The selectivity of acrolein or methacrolein formation will regularly be $\geq 94$ mol %, or $\geq 95$ mol %, or $\geq 96$ mol %, or $\geq 97$ mol %. Of course, very low hotspot temperatures are desired.

Overall, the annular unsupported catalysts obtainable in accordance with the invention bring about both an increased activity and an increased selectivity of target product formation.

Finally, it is emphasized that the annular unsupported catalysts obtainable in accordance with the invention also have advantageous fracture behavior in the course of reactor charging. Their pressure drop behavior is also advantageous. Otherwise, the annular unsupported catalysts obtainable in accordance with the invention are quite generally suitable as catalysts having increased activity and selectivity for catalytic partial oxidations in the gas phase of organic compounds such as lower (for example containing from 3 to 6 (i.e. 3, 4, 5, or 6) carbon atoms) alkanes, alkanols, alkanals, alkenes and alkenals to olefinically unsaturated aldehydes and/or carboxylic acids, and also the appropriate nitrites (ammoxidation, in particular of propene to acrylonitrile and of 2-methylpropene or tert-butanol (or its methyl ether) to methacrylonitrile) and also for catalytic oxidative dehydrogenations in the gas phase of organic compounds (for example containing 3, 4, 5, or 6 carbon atoms).

Particularly advantageous stoichiometries for the process according to the invention are:
a) $[Bi_2W_2O_9.2WO_3]_{0.5}[Mo_{12}Co_{5.5}Fe_{2.94}Si_{1.59}K_{0.08}O_x]_1$;
b) $Mo_{12}Ni_{6.5}Zn_2Fe_2Bi_1P_{0.0065}K_{0.06}O_x.10SiO_2$;
c) $Mo_{12}Co_7Fe_{2.94}Bi_{0.6}Si_{1.59}K_{0.08}O_x$;
d) as per multimetal oxide 11 unsupported catalyst according to Example 1 of DE-A 197 46 210; and
e) as per Example 1c of EP-A 015 565.

The bismuth content of the active compositions obtainable in accordance with the invention may also be adjusted as described in DE-A 100 63 162. In this method, a solution or suspension is generated from starting compounds of the elemental constituents of the desired active composition, said solution or suspension containing the total amount of elemental constituents other than Bi required to prepare the active composition, but only a portion of the Bi required to prepare the active composition, the solution or suspension is dried to obtain a dry mass and the remaining amount of Bi additionally required to form the active composition is incorporated into this dry mass in the form of a starting compound of Bi, as described in DE-A 100 63 162, to obtain a shapeable mixture (for example as in the example of DE-A 100 63 162), the shapeable mixture is shaped to an annular shaped unsupported catalyst body in the inventive manner (optionally after adding shaping and/or reinforcing assistants), and this is then converted to the desired annular unsupported catalyst by thermal treatment (for example as in Example 1 of DE-A 100 63 162). The stoichiometries (especially of the examples) and thermal treatment conditions of this (aforementioned) document are likewise particularly suitable in accordance with the invention. This is especially true of the stoichiometry $Mo_{12}Bi_{1.0}Fe_3Co_7Si_{1.6}K_{0.08}$.

The start-up of a fresh catalyst charge comprising annular unsupported catalysts obtainable in accordance with the invention may be effected as described in DE-A 10337788. In general, activity and selectivity of the target product formation initially increase with the operating time of the catalyst charge. This conditioning may be accelerated by carrying it out at substantially uniform conversion under increased hourly space velocity on the catalyst charge of starting reaction gas mixture, and, after substantially completed conditioning, reducing the hourly space velocity to its target value.

It is surprising that the ratio R of apparent mass density to true mass density p (as defined in EP-A 1340538) in the annular unsupported catalysts obtainable in accordance with the invention is generally >0.55. R is usually ≦0.9 or ≦0.8 and ≦0.6 or ≧0.65.

$R = 1/(1+V \cdot p)$.

V is the total pore volume.

EXAMPLES AND COMPARATIVE EXAMPLES

A) Preparation of Annular Unsupported Catalysts Having the Following Stoichiometry S1 of the Active Composition: $Mo_{12}Co_7Fe_{2.94}Bi_{0.6}Si_{1.59}K_{0.08}O_x$ At 60° C., 213 kg of ammonium heptamolybdate tetrahydrate (81.5% by weight of $MoO_3$) were dissolved in 600 l of water. 0.97 kg of a 46.8% by weight aqueous potassium hydroxide solution at 20° C. was stirred into this solution while maintaining the 60° C. (to obtain a solution A).

A second solution B was prepared by adding 116.25 kg of an aqueous iron(III) nitrate solution (14.2% by weight of Fe) at 20° C. with stirring to 333.7 kg of an aqueous cobalt(II) nitrate solution (12.4% by weight of Co) at 30° C. On completion of addition, stirring was continued at 30° C. for 30 min. Afterward, 112.3 kg of an aqueous bismuth nitrate solution (11.2% by weight of Bi) at 20° C. were stirred in to obtain solution B. Within 30 min., solution B was stirred into solution A at 60° C. 15 min. after completion of stirring-in, 19.16 kg of silica sol (LUDOX® from Dupont, 46.80% by weight of $SiO_2$, density: from 1.36 to 1.42 g/cm$^3$, pH=from 8.5 to 9.5, alkali content max. 0.5% by weight) were added at 60° C. to the resulting slurry. While maintaining 60° C., stirring was continued for a further 15 min. The resulting slurry was then spray-dried in a countercurrent process (gas inlet temperature: 400±10° C., gas outlet temperature: 140±5° C.) to obtain a spray powder whose ignition loss (3 h at 600° C. under air) was 30% of its weight. The particle size of the spray powder was a substantially uniform 30 μm.

In each case an additional 1.5% by weight (based on the amount of spray powder) of finely divided graphite (sieve analysis: min. 50% by weight <24 μm, max. 10% by weight ≧24 μm and ≦48 μm, max. 5% by weight ≧48 μm, BET surface area: from 6 to 13 m$^2$/g) of the TIMREX P44 type from Timcal AG (San Antonio, US) were mixed into portions of the resulting spray powder. The dry mixture resulting in each case was coarsened by precompaction to a substantially uniform particle size of from 400 μm to 1 mm by means of a compactor from Hosokawa Bepex GmbH (D-74211 Leingarten) of the K 200/100 compactor type under the conditions of gap width 2.8 mm, sieve width 1.0 mm, lower particle size sieve width 400 μm, target compressive force 60 kN and screw rotation rate from 65 to 70 rpm. The compactate had a hardness of 10 N.

The compactate was subsequently mixed with, based on its weight, a further 2% by weight of the same graphite and subsequently compressed in a Kilian rotary tableting press of the Rx73 type from Kilian, D-50735 Cologne, under a nitrogen atmosphere to give annular shaped unsupported catalyst precursor bodies having uncurved top surface and of the geometry 5 mm×3 mm×2 mm (E×L×I) and having varying side crushing strength.

The resulting shaped unsupported catalyst precursor bodies and their side crushing strengths were:
EUP 1: 15 N;
EUP 2: 20 N;
CUP 1: 25 N.

For final thermal treatment, in each case 1900 g of the shaped unsupported catalyst precursor bodies were charged in a heatable forced-air chamber (capacity 0.12 m$^3$, 2 Nm$^3$ (STP) of air/min.). Subsequently, the temperature in the bed was changed as follows:
increased from 25° C. to 160° C. at 1° C./min.;
then held at 160° C. for 100 min.;
afterward increased from 160° C. to 200° C. at 3° C./min.;
then held at 200° C. for 100 min.;
afterward increased from 200° C. to 230° C. at 2° C./min.;
then held at 230° C. for 100 min.;
afterward increased from 230° C. to 270° C. at 3° C./min.;
then held at 270° C. for 100 min.;
afterward increased to 380° C. at 1° C./min.;
then held at 380° C. for 4.5 h;
afterward increased to 430° C. at 1° C./min.;
then held at 430° C. for 4.5 h;
afterward increased to 500° C. at 1° C./min.;
then held at 500° C. for 9 h;
afterward cooled to 25° C. within 4 h.

The following annular unsupported catalysts were obtained from the annular shaped unsupported catalyst precursors (the first letter E stands in each case for example, the first letter C for comparative example):
EUP 1→EUC 1;
EUP 2→EUC 2; and
CUP 1→CUC 1.

The parameters S, V, the significant pore diameter $d^{max}$ which makes the greatest contribution to the total pore volume and the percentage of those pore diameters in the total pore volume whose diameters are >0.1 and <1 μm, of these annular unsupported catalysts were as follows:

EUC 1: S=6.4 cm²/g; V=0.32 cm³/g; $d^{max}$=0.32 µm; $V^{0.1}_{1}$_%=91%.

EUC 2: S=6.8 cm²/g; V=0.34 cm³/g; $d^{max}$=0.36 µm; $V^{0.1}_{1}$_%=87%.

Figure 2:
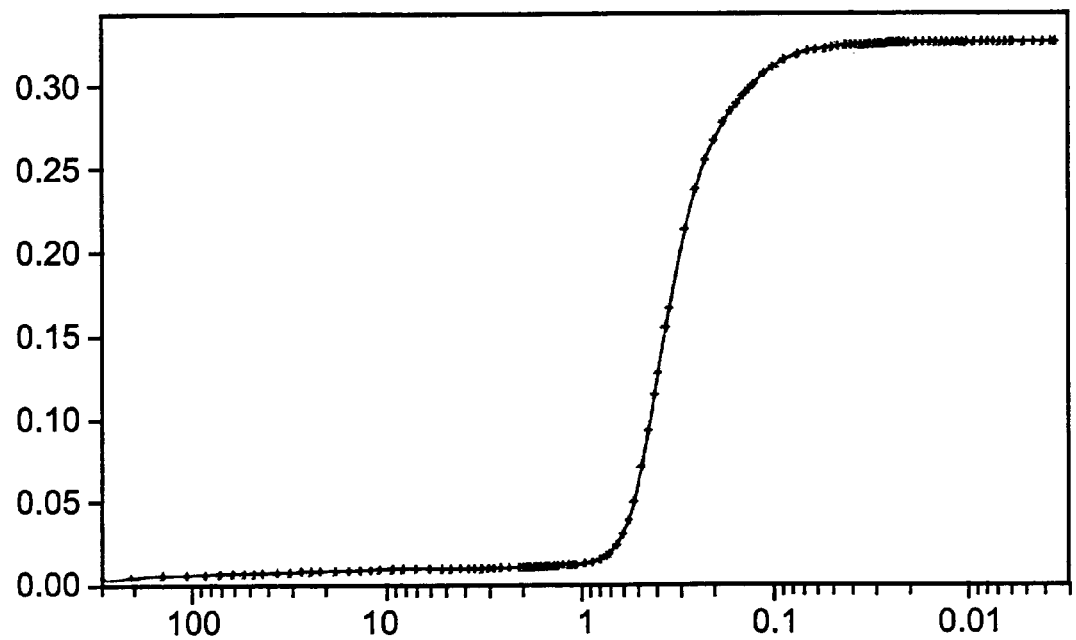
Figure 3:
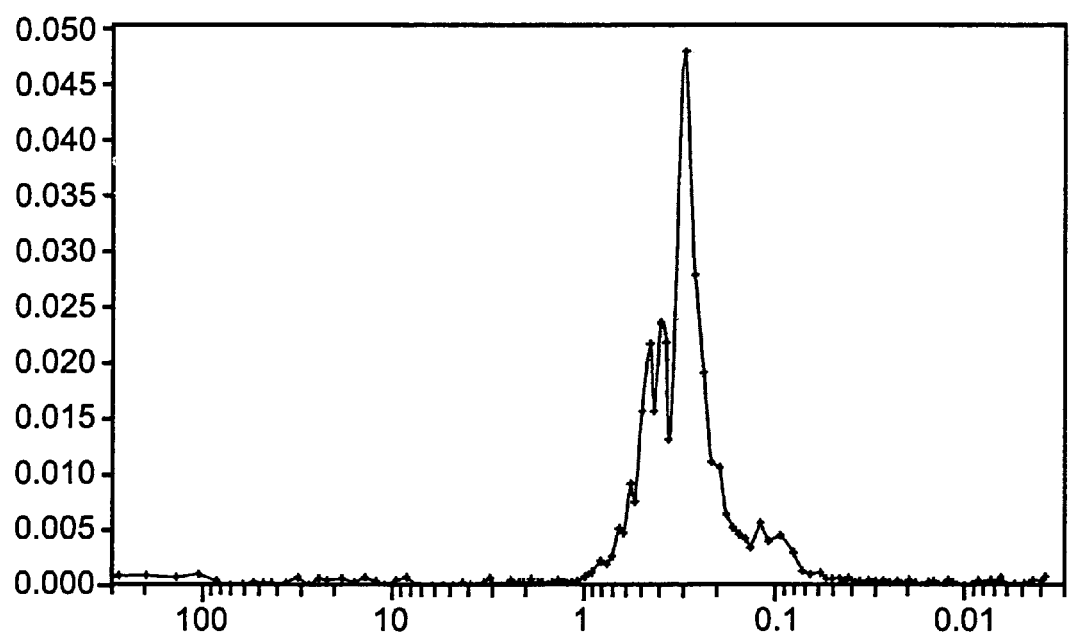
FIGS. 3 and 4 show the pore distribution of the annular unsupported catalyst EUC2.
Figure 4:
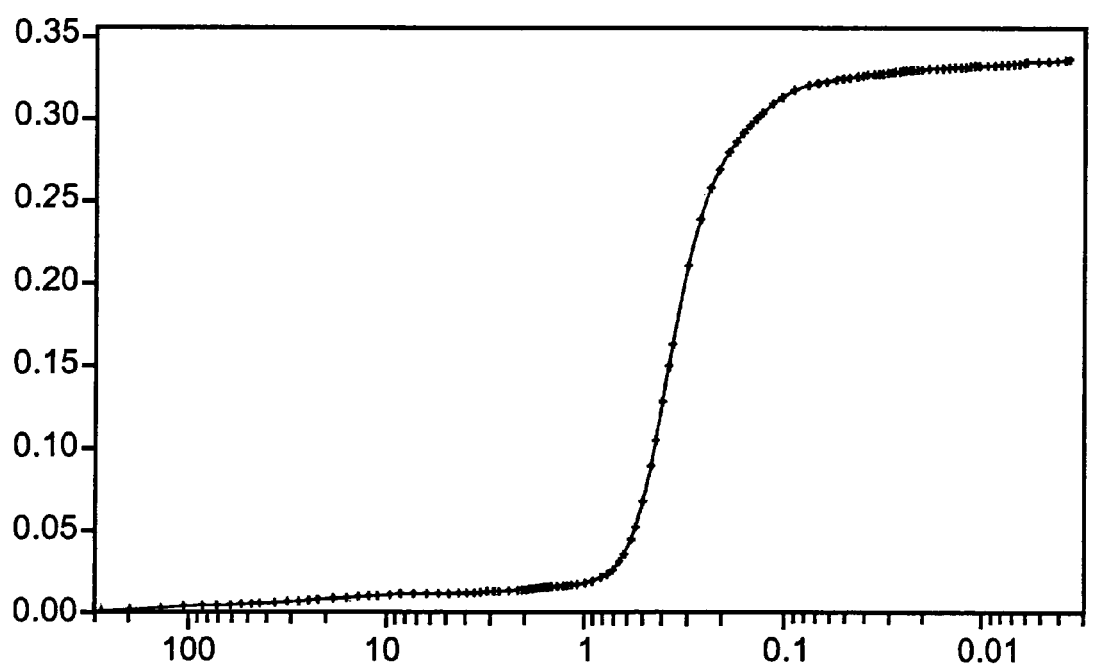

FIGS. 1(3) and 2(4) also show the pore distribution of the annular unsupported catalyst EUC1 (EUC2). In FIG. 1(3), the abscissa shows the pore diameter in µm and the ordinate the different contribution in ml/g of the particular pore diameter to the total pore volume. In FIG. 2(4), the abscissa likewise shows the pore diameter in µm and the ordinate the integral over the individual contributions of the individual pore diameters to the total pore volume in ml/g.

(Instead of carrying out the thermal treatment as described, it may also be carried out as described in Example 3 of DE-A 10046957 by means of a belt calcining apparatus; the chambers have a surface area (with a uniform chamber length of 1.40 m) of 1.29 m² (decomposition, chambers 1-4) and 1.40 m² (calcining, chambers 5-8) and are flowed through from below through the coarse-mesh belt by 75 m³ (STP) of forced air which is aspirated by means of rotating ventilators; within the chambers, the temporal and local deviation of the temperature from the target value was always ≦2° C.; the annular shaped unsupported catalyst bodies are conducted through the chambers in a layer height of from 50 mm to 70 mm; otherwise, the procedure is as described in Example 3 of DE-A 10046957; like the annular unsupported catalysts EUC1, EUC2 and CUC1, the resulting annular unsupported catalysts may be used for the catalytic partial oxidation in the gas phase of propene to acrolein described hereinbelow under C)).

B) Preparation of Annular Unsupported Catalysts Having The Following Stoichiometry S2 of the Active Composition

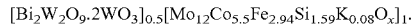

1. Preparation of a Starting Composition 1

209.3 kg of tungstic acid (72.94% by weight of W) were stirred in portions into 775 kg of an aqueous bismuth nitrate solution in nitric acid (11.2% by weight of Bi; free nitric acid from 3 to 5% by weight; mass density: 1.22 to 1.27 g/ml) at 25° C. The resulting aqueous mixture was subsequently stirred at 25° C. for a further 2 h and subsequently spray-dried.

The spray-drying was effected in a rotating disk spray tower in countercurrent at a gas inlet temperature of 300±10° C. and a gas outlet temperature of 100±10° C. The resulting spray powder (particle size a substantially uniform 30 µm) which had an ignition loss of 12% by weight (ignite at 600° C. under air for 3 h) was subsequently converted to a paste in a kneader using 16.8% by weight (based on the powder) of water and extruded by means of an extruder (rotational moment: ≦50 Nm) to extrudates of diameter 6 mm. These were cut into sections of 6 cm, dried under air on a 3-zone belt dryer at a residence time of 120 min at temperatures of 90-95° C. (zone 1), 115° C. (zone 2) and 125° C. (zone 3), and then thermally treated at a temperature in the range from 780 to 810° C. (calcined; in a rotary tube oven flowed through by air (0.3 mbar of reduced pressure, capacity 1.54 m³, 200 m³ (STP) of air/h)). When precisely adjusting the calcination temperature, it is essential that it has to be directed to the desired phase composition of the calcination product. The desired phases are $WO_3$ (monoclinic) and $Bi_2W_2O_9$; the presence of $\gamma$-$Bi_2WO_6$ (Russellite) is undesired. Therefore, should the compound $\gamma$-$Bi_2WO_6$ still be detectable by a reflection at a reflection angle of 2Θ=28.4° (CuKα-radiation) in the x-ray powder diffractogram after the calcination, the preparation has to be repeated and the calcination temperature increased within the temperature range specified or the residence time increased at constant calcination temperature, until the disappearance of the reflection is achieved. The preformed calcined mixed oxide obtained in this way was ground so that the $X_{50}$ value (cf. Ullmann's Encyclopedia of Industrial Chemistry, 6th Edition (1998) Electronic Release, Chapter 3.1.4 or DIN 66141) of the resulting particle size was 5 mm. The ground material was then mixed with 1% by weight (based on the ground material) of finely divided $SiO_2$ from Degussa of the SIPERNAT® type (bulk density 150 g/l; $X_{50}$ value of the $SiO_2$ particles was 10 µm, the BET surface area was 100 m²/g).

2. Preparation of a Starting Composition 2

A solution A was prepared by dissolving 213 kg of ammonium heptamolybdate tetrahydrate (81.5% by weight of $MoO_3$) at 60° C. with stirring in 600 l of water and the resulting solution was admixed while maintaining the 60° C. and stirring with 0.97 kg of an aqueous potassium hydroxide solution (46.8% by weight of KOH) at 20° C.

A solution B was prepared by introducing 116.25 kg of an aqueous iron(III) nitrate solution (14.2% by weight of Fe) at 60° C. into 262.9 kg of an aqueous cobalt(II) nitrate solution (12.4% by weight of Co). Subsequently, while maintaining the 60° C., solution B was continuously pumped into the initially charged solution A over a period of 30 minutes. Subsequently, the mixture was stirred at 60° C. for 15 minutes. 19.16 kg of a LUDOX® silica gel from Dupont (46.80% by weight of $SiO_2$, density: from 1.36 to 1.42 g/ml, pH from 8.5 to 9.5, max. alkali content 0.5% by weight) were then added to the resulting aqueous mixture, and the mixture was stirred afterward at 60° C. for a further 15 minutes.

Subsequently, the mixture was spray-dried in countercurrent in a rotating disk spray tower (gas inlet temperature: 400±10° C., gas outlet temperature: 140±5° C.). The resulting spray powder had an ignition loss of approx. 30% by weight (ignite under air at 600° C. for 3 h) and a substantially uniform particle size of 30 µm.

3. Preparation of the Multimetal Oxide Active Composition

The starting composition 1 was mixed homogeneously with the starting composition 2 in the amounts required for a multimetal oxide active composition of the stoichiometry

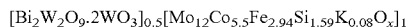

in a mixer having bladed heads. Based on the aforementioned overall composition, an additional 1% by weight of finely divided graphite from Timcal AG (San Antonio, US) of the TIMREX P44 type (sieve analysis: min. 50% by weight <24 µm, max. 10% by weight ≧24 µm and ≦48 µm, max. 5% by weight >48 µm, BET surface area: from 6 to 13 m²/g) were mixed in homogeneously. The resulting mixture was then conveyed in a compactor (from Hosokawa Bepex GmbH, D-74211 Leingarten) of the K200/100 compactor type having concave, fluted smooth rolls (gap width: 2.8 mm, sieve width: 1.0 mm, lower particle size sieve width: 400 µm, target compressive force: 60 kN, screw rotation rate: from 65 to 70 revolutions per minute). The resulting compactate had a hardness of 10 N and a substantially uniform particle size of from 400 µm to 1 mm.

The compactate was subsequently mixed with, based on its weight, a further 2% by weight of the same graphite and subsequently compressed in a Kilian rotary tableting press of the Rx73 type from Kilian, D-50735 Cologne, under a nitrogen atmosphere to give annular shaped unsupported catalyst precursor bodies of varying geometry (E×L×I) having varying side crushing strength.

The resulting shaped unsupported catalyst precursor bodies, their geometries and their side crushing strengths were:

| EUP3: | 5 mm × 3 mm × 2 mm; | 19 N (mass: 129 mg). |
|---|---|---|
| EUP4: | 5 mm × 3 mm × 3 mm; | 16 N. |
| EUP5: | 5 mm × 3 mm × 3 mm; | 17 N. |
| EUP6: | 5.5 mm × 3 mm × 3.5 mm; | 14 N. |
| EUP7: | 5.5 mm × 3 mm × 3.5 mm; | 15.5 N. |
| EUP8: | 6 mm × 3 mm × 4 mm; | 13 N. |
| EUP9: | 6 mm × 3 mm × 4 mm; | 16.3 N. |
| CUP2: | 6.5 mm × 3 mm × 4.5 mm; | 11 N. |
| EUP10: | 6.5 mm × 3 mm × 4.5 mm; | 15.6 N. |
| CUP3: | 7 mm × 3 mm × 5 mm; | 11.7 N. |
| EUP11: | 7 mm × 3 mm × 5 mm; | 16.3 N. |
| CUP4: | 5 mm × 3 mm × 2 mm; | 10.5 N |

Figure 5:
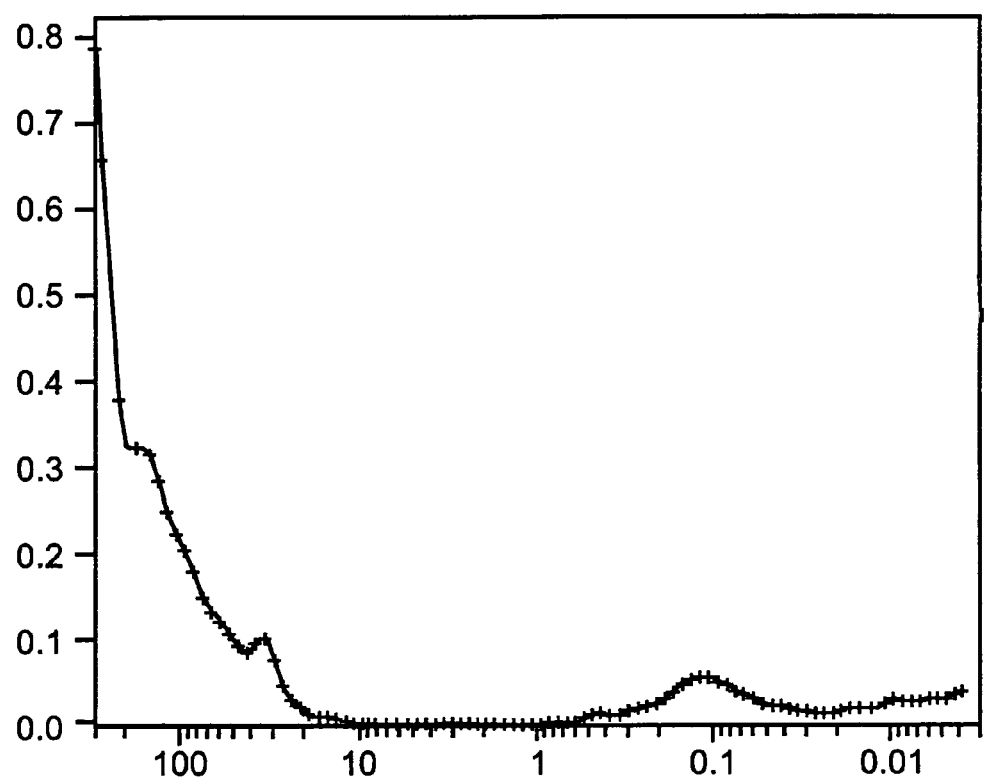
FIGS. 5 and 6 show the pore distribution of the annular unsupported catalyst EUP3.
Figure 6:
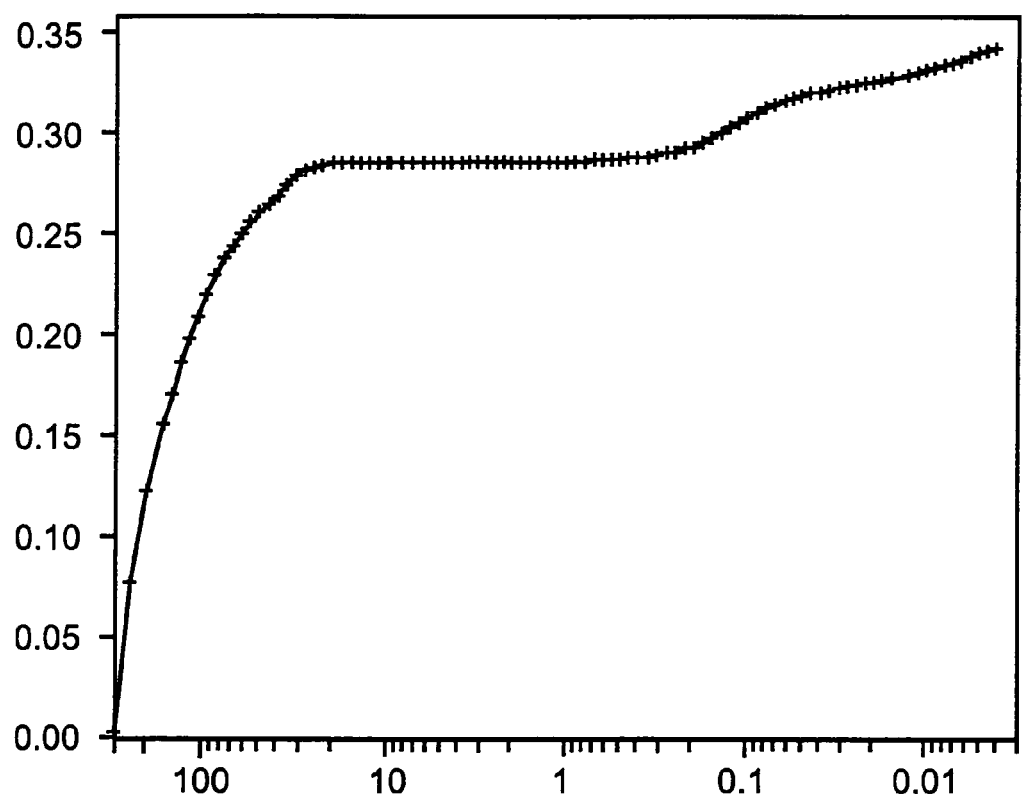

FIGS. 5(6) shows the pore distribution in the annular shaped unsupported catalyst precursor body EUP3. The axis title of FIG. 5 corresponds to that of FIG. 1 and the axis title of FIG. 6 corresponds to that of FIG. 2.

For the final thermal treatment, in each case 1000 g of the shaped unsupported catalyst precursor bodies were heated in a muffle furnace flowed through by air (capacity 60 l, 1 l/h of air per gram of shaped unsupported catalyst precursor body) initially from room temperature (25° C.) to 190° C. at a heating rate of 180° C./h. This temperature was maintained for 1 h and then increased to 210° C. at a heating rate of 60° C./h. The temperature of 210° C. was in turn maintained over 1 h before it was increased to 230° C. at a heating rate of 60° C./h. This temperature was likewise maintained for 1 h before it was increased to 265° C., again at a heating rate of 60° C./h. The temperature of 265° C. was subsequently likewise maintained over 1 h. Afterward, the furnace was initially cooled to room temperature and the decomposition phase thus substantially completed. The furnace was then heated to 465° C. at a heating rate of 180° C./h and this calcination temperature maintained over 4 h.

The annular shaped unsupported catalyst precursor bodies were used to obtain the following annular unsupported catalysts (the first letter E stands in each case for example, the first letter C in each case for comparative example):

| | S [cm²/g] | V [cm³/g] | $d^{max}$ [μm] | $V^{0.1}_1$- % | R |
|---|---|---|---|---|---|
| EUP3 → EUC3 | 7.6 | 0.27 | 0.6 | 79 | 0.66 |
| EUP4 → EUC4 | 6.9 | 0.23 | 0.45 | 70 | — |
| EUP5 → EUC5 | — | — | — | — | — |
| EUP6 → EUC6 | 7.45 | 0.21 | 0.40 | 74 | — |
| EUP7 → EUC7 | 7.95 | 0.205 | 0.39 | 73 | 0.68 |
| EUP8 → EUC8 | 7.6 | 0.22 | 0.45 | 74 | — |
| EUP9 → EUC9 | 9.61 | 0.22 | 0.30 | 70 | 0.68 |
| CUP2 → CUC2 | — | — | — | — | — |
| EUP10 → EUC10 | — | — | — | — | — |
| CUP3 → CUC3 | — | — | — | — | — |
| EUP11 → EUC11 | — | — | — | — | — |
| CUP4 → EUC4 | 10.2 | 0.19 | 0.28 | 64 | — |

In addition, the table above contains values for the specific surface area S, the total pore volume V, the pore diameter $d^{max}$ which makes the greatest contribution to the total pore volume, and the percentage of those pore diameters in the total pore volume whose diameters are >0.1 and <1 μm, and R values.

Figure 7:
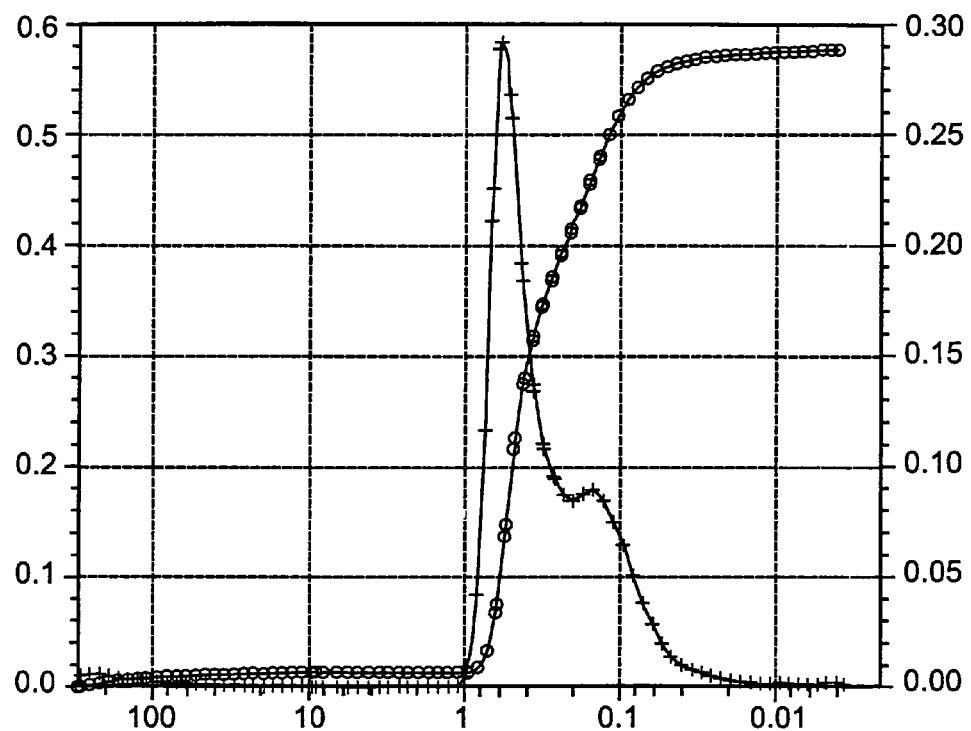
FIGS. 7-10 show the pore distribution of the annular unsupported catalyst EUC3.
Figure 8:
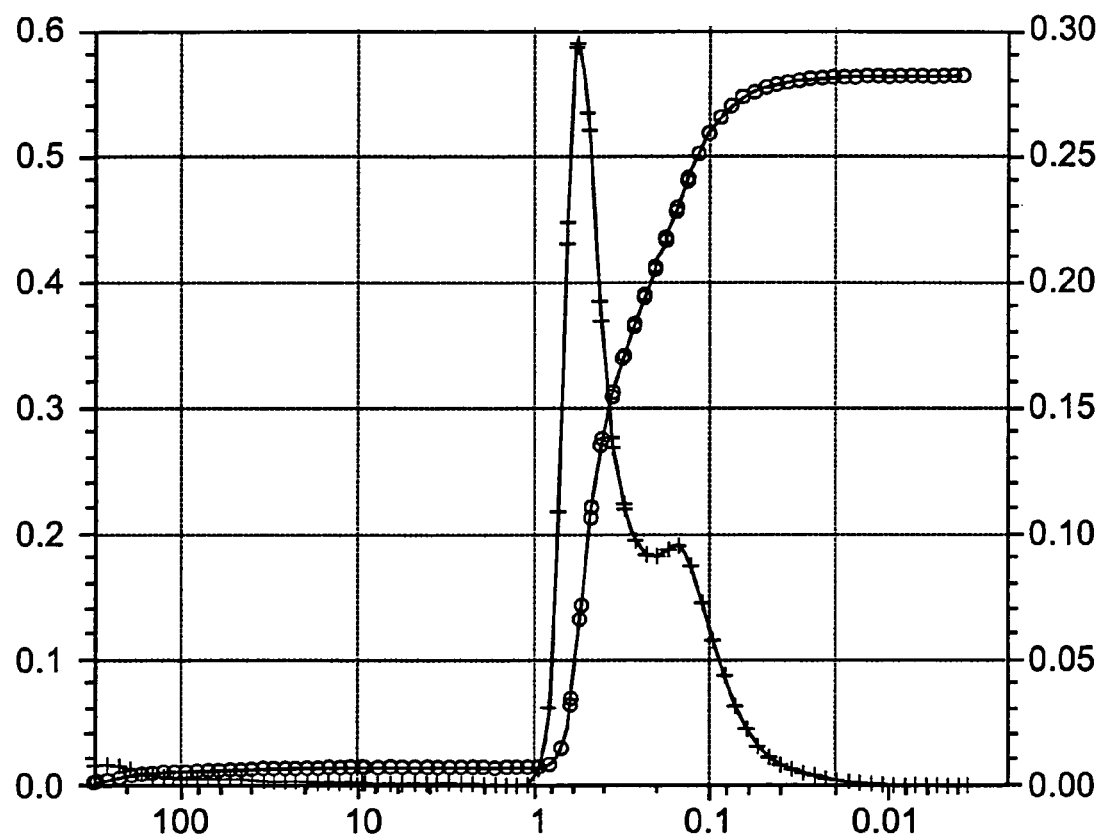
Figure 9:
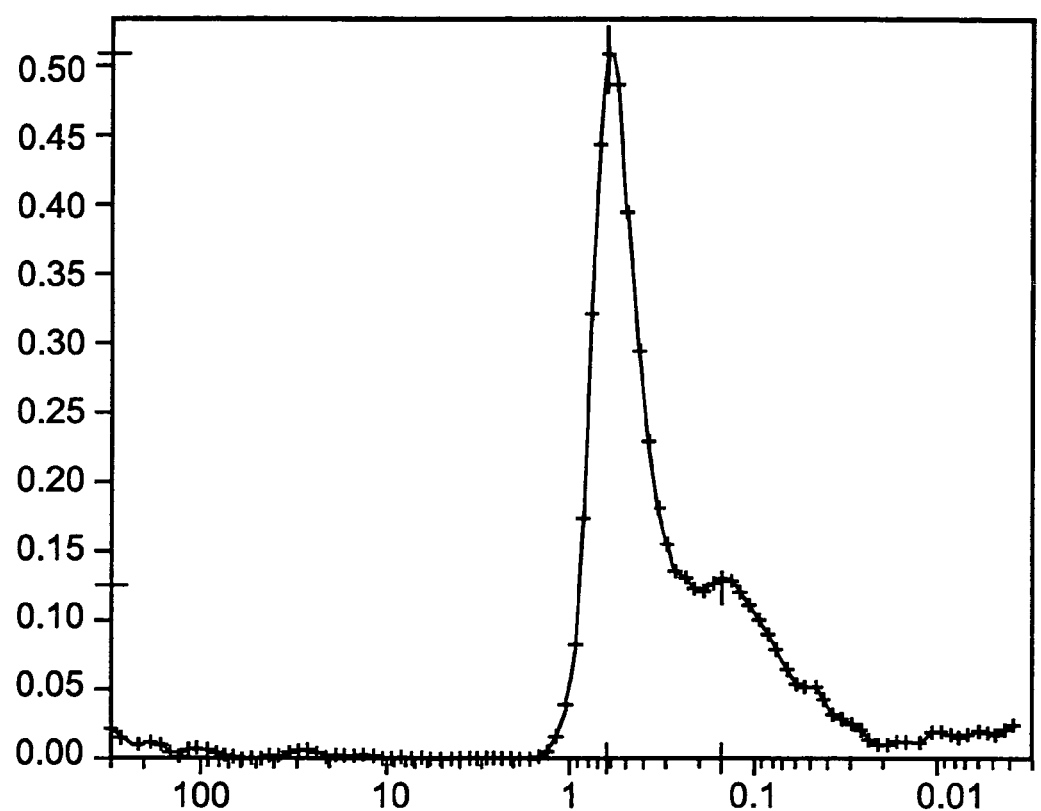
Figure 10:
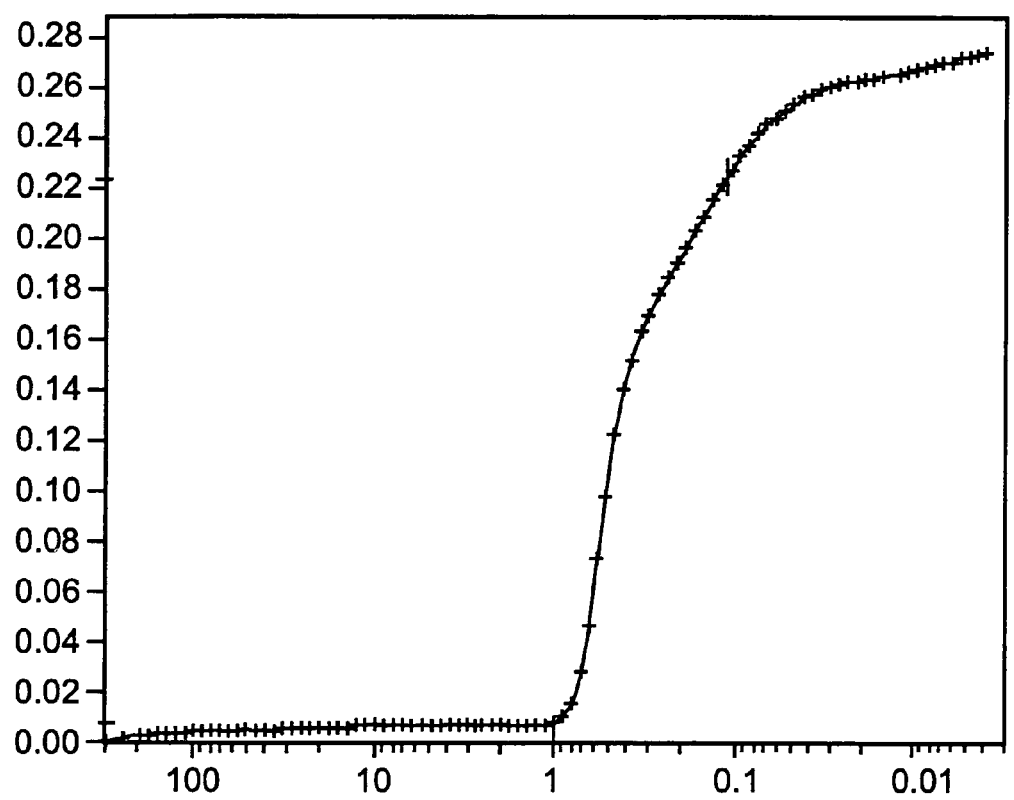

FIGS. 7 and 8 also show the pore distribution of the annular unsupported catalyst EUC3 for two independent reproductions. On the abscissa is plotted the pore diameter in μm. On the left ordinate is plotted the logarithm of the different contribution in mug of the particular pore diameter to the total pore volume (+curve). The maximum indicates the pore diameter having the greatest contribution to the total pore volume. On the right ordinate is plotted, in ml/g, the integral over the individual contributions of the individual pore diameters to the total pore volume (O curve). The endpoint is the total pore volume. FIGS. 9 and 10 show the pore distribution of a further reproduction of EUC3 with the same axis titling as in FIG. 7, 8.

Figure 11:
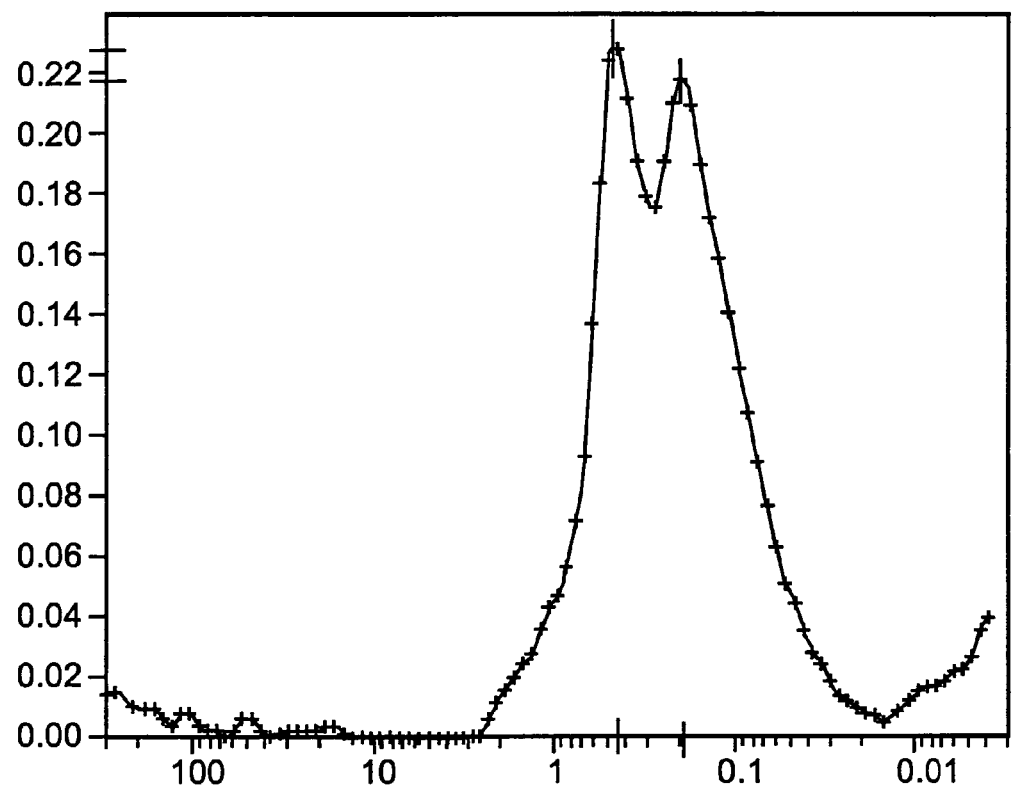
FIGS. 11 and 12 show the pore distribution of the annular unsupported catalyst EUC4.
Figure 12:
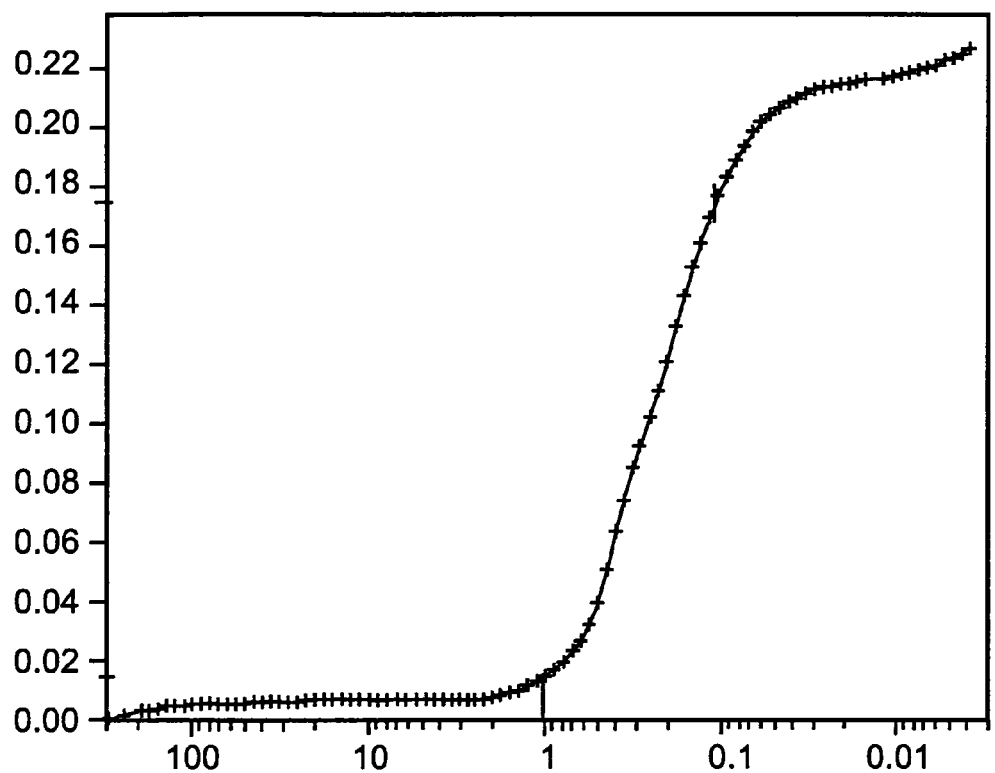
Figure 13:
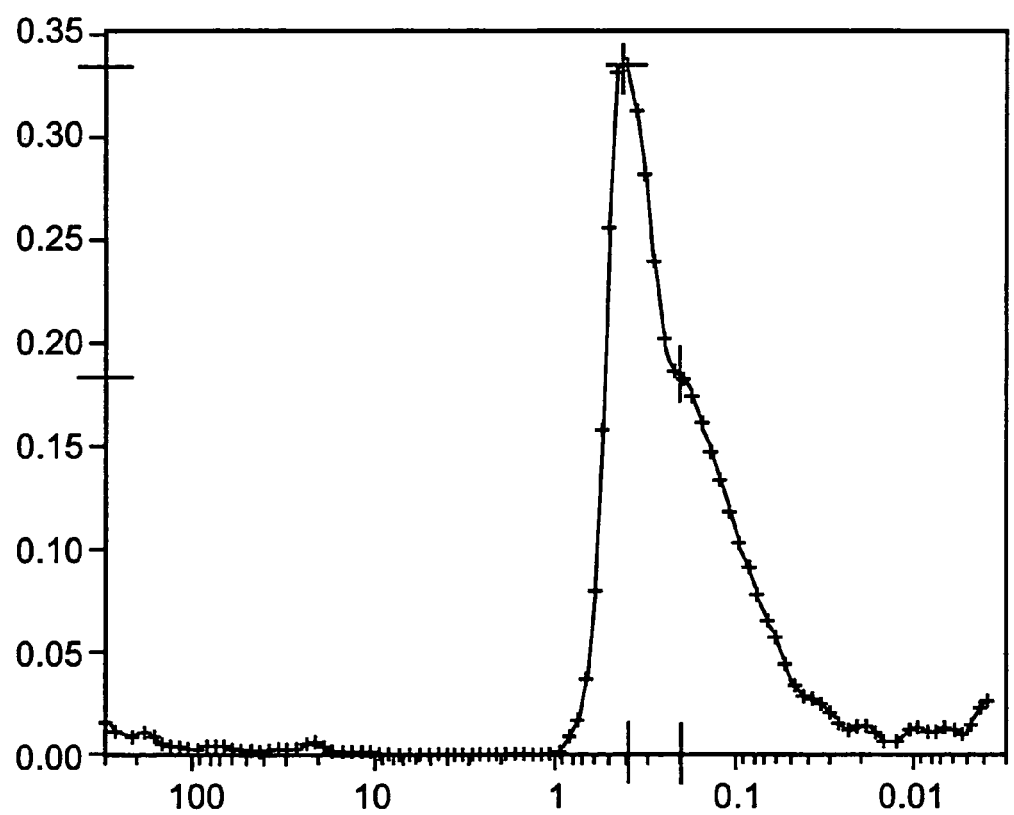
FIGS. 13 and 14 show the pore distribution of the annular unsupported catalyst EUC6.
Figure 14:
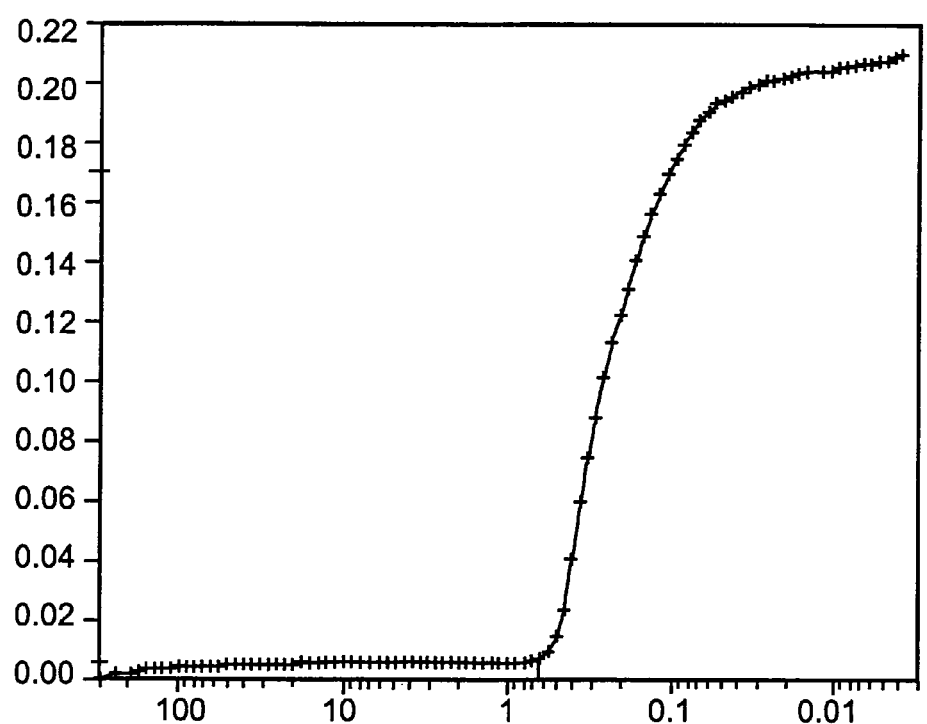
Figure 15:
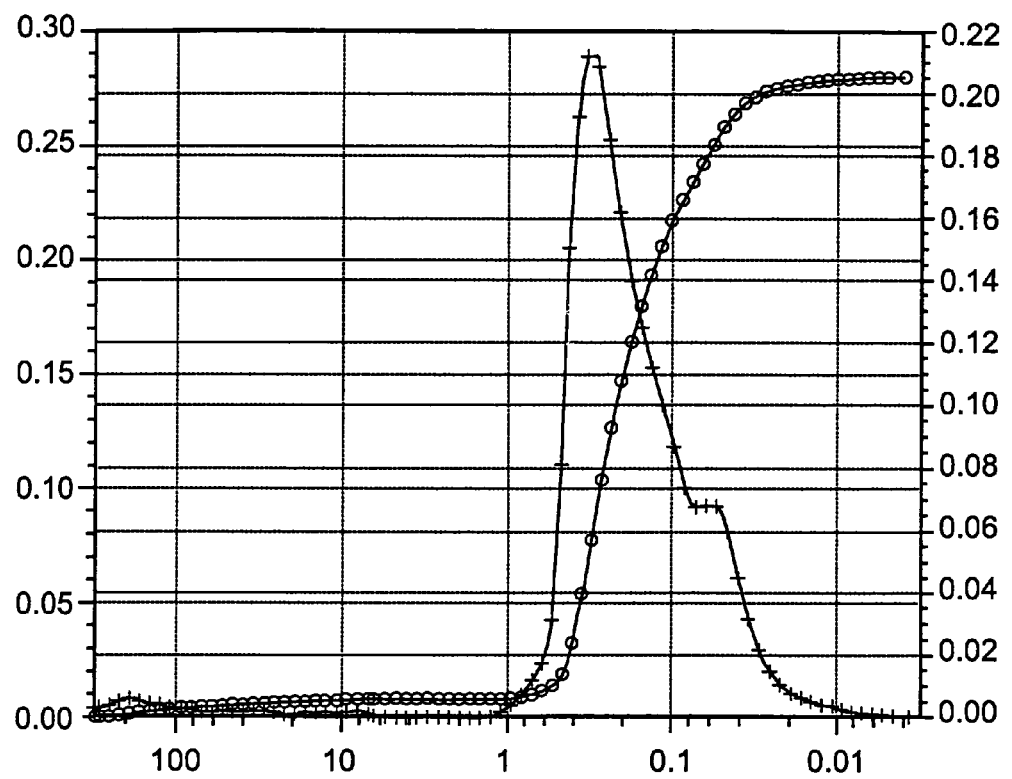
FIG. 15 shows the pore distribution of the annular unsupported catalyst EUC7.
Figure 16:
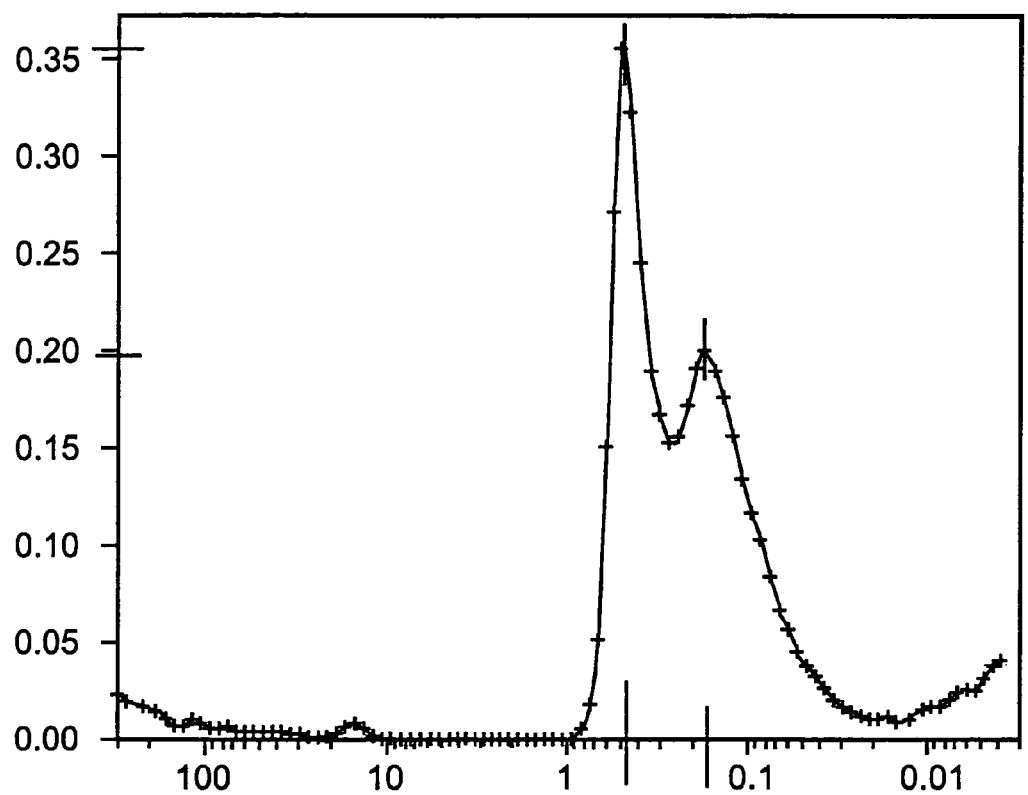
FIGS. 16 and 17 show the pore distribution of the annular unsupported catalyst EUC8.
Figure 17:
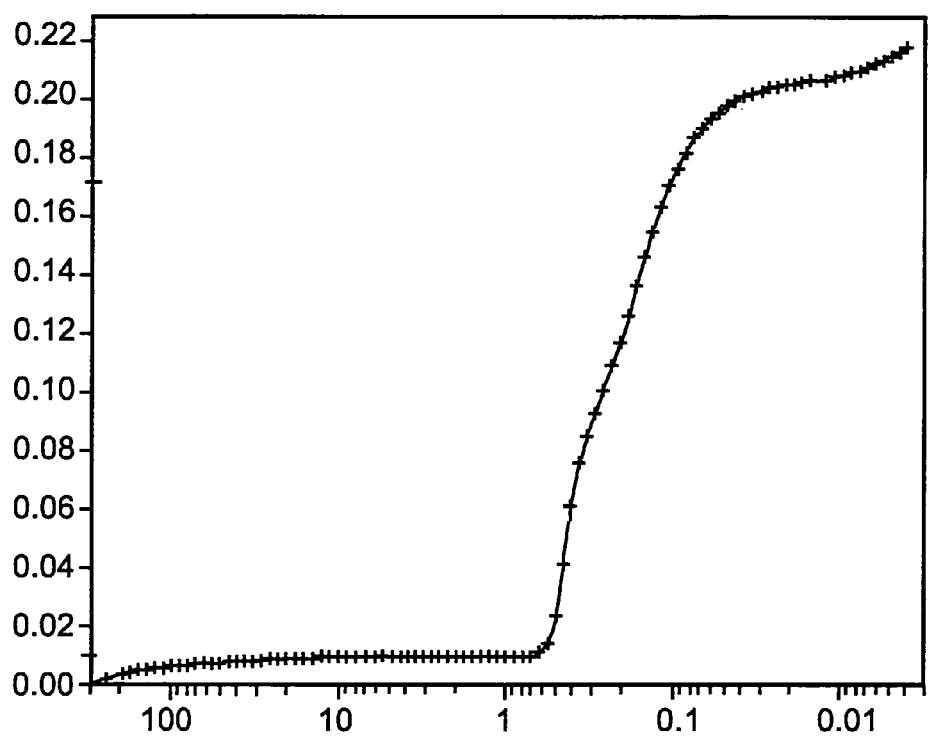
Figure 18:
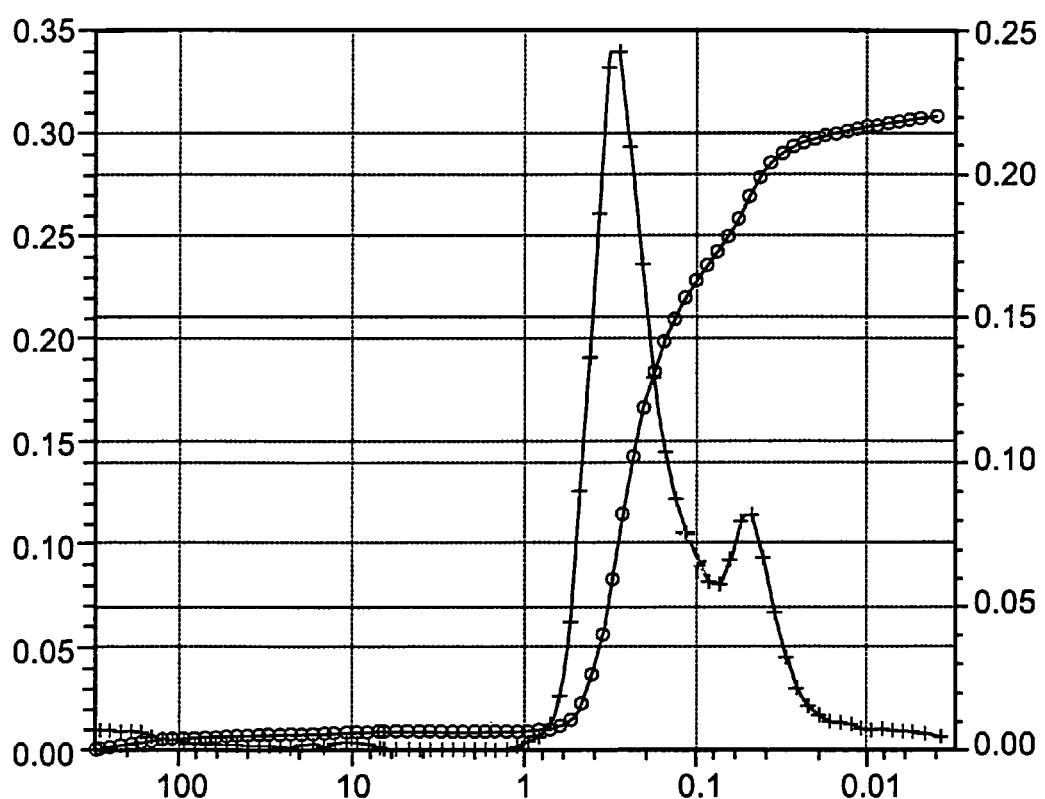
FIG. 18 shows the pore distribution of the annular unsupported catalyst EUC9.

Corresponding figures are FIGS. 11, 12 (EUC4), FIGS. 13, 14 (EUC6), FIG. 15 (EUC7), FIGS. 16, 17 (EUC8) and FIG. 18 (EUC9).

Instead of carrying out the thermal treatment as described, it may also be carried out by means of a belt calcining apparatus as described in Example 1 of DE-A 10046957 (however, the bed height in the decomposition (chambers 1 to 4) is advantageously 44 mm at a residence time per chamber of 1.46 h and, in the calcination (chambers 5 to 8), it is advantageously 130 mm at a residence time of 4.67 h); the chambers have a surface area (with a uniform chamber length of 1.40 m) of 1.29 m² (decomposition) and 1.40 m² (calcination) and are flowed through from below through the coarse-mesh belt by 75 m³/(STP)/h of forced air which is aspirated by means of rotating ventilators. Within the chambers, the temporal and local deviation of the temperature from the target value is always ≦2° C. Otherwise, the procedure is as described in Example 1 of DE-10046957. The resulting annular unsupported catalysts, like the annular unsupported catalysts EUC3 to EUC4, may be used for the catalytic partial oxidation in the gas phase of propene to acrolein described hereinbelow.

As a further alternative, the thermal treatment may be carried out in a forced-air furnace (for example in a KA-040/006-08 EW.OH laboratory chamber furnace from Elino or a K 750 from Heraeus) in such a way that the furnace is heated to 270° C. within 6 h and the temperature of 270° C. is subsequently maintained until the forced air is free of nitrous gases. Subsequently, the furnace is heated to a temperature of from 430° C. to 460° C. (preferably to 438° C.) within 1.5 h and this temperature is maintained for 10 h. The air purge flow is 800 l(STP)/h. 1000 g of annular shaped unsupported catalyst precursor bodies are introduced into a rectangular wire basket (10 cm high, area 14 cm×14 cm) in a bed height of approx. 4 cm. The remaining surface area of the carrying basket is covered in an appropriate bed height with steatite rings (as always in the examples and comparative examples, of the C220 type from Ceram Tec, Germany) of the same geometry.

These thermal treatment conditions may also be employed on the annular shaped unsupported catalyst precursor bodies EUP1, EUP2 and CUP1. All resulting annular unsupported catalysts may be used in the catalytic partial oxidation in the gas phase described by way of example under C).

C) Testing of the Annular Unsupported Catalysts Prepared in A) and B) for the Heterogeneously Catalyzed Partial Oxidation of Propene to Acrolein 1. Experimental Arrangement A reaction tube (V2A steel; external diameter 21 mm, wall thickness 3 mm, internal diameter 15 mm, length 100 cm) was charged from top to bottom in the flow direction as follows:

Section 1: length 30 cm

Steatite rings of geometry 5 mm×3 mm×2 mm (external diameter×length×internal diameter) as a preliminary bed.

Section 2: length 70 cm

Catalyst charge of the annular unsupported catalysts prepared in A) and B).

The reaction tube was heated with the aid of a salt bath sparged with nitrogen.

2. Experimental Procedure

The experimental arrangement described, in each case freshly prepared, was in each case charged continuously with a charge gas mixture (mixture of air, polymer-grade propylene and nitrogen) of the composition:

5% by volume of propene,

10% by volume of oxygen and as the remainder up to 100% by volume, $N_2$ and the hourly space velocity and the thermosetting of the reaction tube was such that the propene conversion C (mol %) on single pass of the charge gas mixture through the reaction tube was continuously about 95 mol %.

The table which follows shows the salt bath temperatures $T_S$ (° C.) and also the acrolein selectivities $S^A$ achieved (mol %) which are required to achieve conversion, as a function of the selected catalyst charge and propene hourly space velocity (PHSV in l (STP)/l·h) thereon. The results reported always relate to the end of an operating time of 120 h. The selectivity $S^{AA}$ of acrylic acid by-production was in the range from 4 to 17 mol %.

| Annular unsupported catalyst | PHSV | $T_s$ | $S^A$ | $S^{AA}$ |
|---|---|---|---|---|
| EUC1 | 50 | 306 | 89.5 | 4.7 |
| EUC2 | 50 | 306 | 89.5 | 4.6 |
| CUC1 | 50 | 309 | 89.0 | 4.0 |
| EUC1 | 75 | 310 | 90.5 | 4.9 |
| EUC2 | 75 | 311 | 90.5 | 4.9 |
| CUC1 | 75 | 313 | 89.8 | 4.5 |
| EUC1 | 100 | 315 | 90.8 | 5.2 |
| EUC2 | 100 | 318 | 91.1 | 5.1 |
| CUC1 | 100 | 321 | 90.5 | 4.8 |
| EUC3 | 50 | 320 | 88.6 | 7.1 |
| EUC4 | 50 | 325 | 86.1 | 8.8 |
| EUC5 | 50 | 322 | 86.6 | 8.9 |
| EUC6 | 50 | 338 | 84.9 | 10.2 |
| EUC7 | 50 | 320 | 90.2 | 5.1 |
| EUC8 | 50 | 343 | 85.0 | 10.3 |
| EUC9 | 50 | 322 | 90.0 | 5.4 |
| CUC2 | 50 | 349 | 83.4 | 12.3 |
| EUC10 | 50 | 333 | 93.1 | 5.4 |
| CUC3 | 50 | 345 | 75.3 | 16.2 |
| EUC11 | 50 | 333 | 87.9 | 7.6 |
| CUC4 | 50 | 337 | 84.3 | 8.6 |

However, the experiments above may also be carried out in a corresponding manner (same target conversion) in a reaction tube of the following type: V2A steel; external diameter 30 mm, wall thickness 2 mm, internal diameter 26 mm, length 350 cm, a thermal tube centered in the middle of the reaction tube (external diameter 4 mm) for accommodating a thermal element by which the temperature may be determined in the reaction tube over its entire length.

In the flow direction, the charge is as follows:

| | |
|---|---|
| Section 1: | length 80 cm |
| | Steatite rings of geometry 7 mm × 7 mm × 4 mm (external diameter × length × internal diameter) as a preliminary bed. |
| Section 2: | length 270 cm |
| | Catalyst charge of the annular unsupported catalysts prepared in A) and B). |

The reaction tube is heated by means of a salt bath pumped in countercurrent.

PHSV is selected at a constant 100. The composition of the starting reaction gas mixture is 5.4% by volume of propene, 10.5% by volume of oxygen, 1.2% by volume of $CO_x$, 81.3% by volume of $N_2$ and 1.6% by volume of $H_2O$.

However, this experimental procedure may also be carried out in a corresponding manner using a catalyst charge whose section 2 has the following configuration (in each case in flow direction):

I. Initially to length 100 cm, a homogeneous mixture of 65% by weight of EUC3 and 35% by weight of steatite rings (5 mm×3 mm×2 mm); then to length 170 cm, a homogeneous mixture of 90% by weight of EUC3 and 10% by weight of steatite rings (5 mm×3 mm×2 mm);

or

II. Initially to length 100 cm, EUC10; then to length 170 cm, EUC3;

or

III. Initially to length 1 00 cm, a homogeneous mixture of 70% by weight of EUC3 and 30% by weight of steatite rings (5 mm×3 mm×2 mm); then to length 170 cm, EUC3.

$T_S$ is selected in all cases in such a way that C-propene=95 mol %.

US Provisional Patent Application No. 60/504207, filed on Sep. 22, 2003, is incorporated into the present application by reference. With reference to the abovementioned teachings, numerous alterations and deviations from the present invention are possible. It may therefore be assumed that the invention, within the scope of the appended claims, may be performed differently than specifically described herein.

We claim:

1. A process for preparing an annular unsupported catalyst having at least one member selected from the group consisting of a curved and uncurved top surface thereof, whose active composition has a stoichiometry of the general formula I $$Mo_{12}Bi_aFe_bX^1_cX^2_dX^3_eX^4_fO_n \qquad (I)$$

where $X^1$=at least one element selected from the group consisting of nickel and cobalt, $X^2$=at least one element selected from the group consisting of thallium, an alkali metal and an alkaline earth metal, $X^3$=at least one element selected from the group consisting of zinc, phosphorus, arsenic, boron, antimony, tin, cerium, lead and tungsten, $X^4$=at least one element selected from the group consisting of silicon, aluminum, titanium and zirconium, a=from 0.2 to 5, b=from 0.01 to 5, c=from 0 to 10, d=from 0 to 2, e=from 0 to 8, f=from 0 to 10 and n = a number which is determined by the valency and frequency of the elements in I other than oxygen,
or a stoichiometry of the general formula II

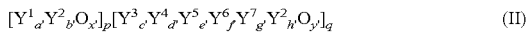 (II)

where
$Y^1$ = only bismuth or bismuth and at least one element selected from the group consisting of tellurium, antimony, tin and copper,
$Y^2$ = molybdenum or molybdenum and tungsten,
$Y^3$ = at least one element selected from the group consisting of an alkali metal, thallium and samarium,
$Y^4$ = at least one element selected from the group consisting of an alkaline earth metal, nickel, cobalt, copper, manganese, zinc, tin, cadmium and mercury,
$Y^5$ = iron or iron and at least one element selected from the group consisting of vanadium, chromium and cerium,
$Y^6$ = at least one element selected from the group consisting of phosphorus, arsenic, boron and antimony,
$Y^7$ = at least one element selected from the group consisting of a rare earth metal, titanium, zirconium, niobium, tantalum, rhenium, ruthenium, rhodium, silver, gold, aluminum, gallium, indium, silicon, germanium, lead, thorium and uranium,
a' = from 0.01 to 8,
b' = from 0.1 to 30,
c' = from 0 to 4,
d' = from 0 to 20,
e' is from >0 to 20,
f' = from 0 to 6,
g' = from 0 to 15,
h' = from 8 to 16,
x', y' = numbers which are determined by the valency and frequency of the elements in II other than oxygen and
p, q = numbers whose p/q ratio is from 0.1 to 10,
and whose annular geometry, without taking into account any existing curvature of the top surface, has a length L of from 2 to 11 mm, an external diameter E of from 2 to 11 mm and a wall thickness W of from 0.75 mm to 1.75 mm,
comprising generating a finely divided shapeable mixture from sources of the elemental constituents of the active composition and, optionally after adding at least one member selected from the group consisting of shaping and reinforcing assistants, compressing this mixture to form annular shaped unsupported catalyst precursor bodies whose top surfaces are at least one member selected from the group consisting of curved and uncurved, and converting these to the annular unsupported catalysts by thermally treating at elevated temperature, wherein
the side crushing strength of the annular shaped unsupported catalyst precursor bodies is ≧12 N and ≦23 N, and wherein
the annular geometry additionally fulfills the condition L/E=from 0.3 to 0.7.

2. A process as claimed in claim 1, wherein the side crushing strength of the annular shaped unsupported catalyst precursor bodies is from ≧13 N to ≦22 N.

3. A process as claimed in claim 1, wherein the side crushing strength of the annular shaped unsupported catalyst precursor bodies is from ≧15 N to ≦20 N.

4. A process as claimed in any of claims 1 to 3, wherein the annular geometry additionally fulfills the condition L/E=from 0.4 to 0.6.

5. A process as claimed in any of claims 1 to 3, wherein the annular geometry additionally fulfills the internal diameter I/external diameter E ratio=from 0.5 to 0.8.

6. A process as claimed in any of claims 1 to 3, wherein the annular geometry additionally fulfills the internal diameter I/external diameter E ratio=from 0.6 to 0.7.

7. A process as claimed in any of claims 1 to 3, wherein L=from 2 to 6 mm.

8. A process as claimed in any of claims 1 to 3, wherein L=from 2 to 4 mm.

9. A process as claimed in any of claims 1 to 3, wherein E=from 4 to 8 mm.

10. A process as claimed in any of claims 1 to 3, wherein E=from 5 to 7 mm.

11. A process as claimed in any of claims 1 to 3, wherein the wall thickness of the annular geometry is from 1 to 1.5 mm.

12. A process as claimed in any of claims 1 to 3, wherein the annular geometry, expressed as E×L×I, is an annular geometry from the group consisting of
a) 5 mm×3 mm×2 mm,
b) 5 mm×3 mm×3 mm,
c) 5.5 mm×3 mm×3.5 mm,
d) 6 mm×3 mm×4 mm,
e) 6.5 mm×3 mm×4.5 mm and
f) 7 mm×3 mm×5 mm.

13. A process as claimed in any of claims 1 to 3, wherein the active composition has a stoichiometry of the general formula I wherein
a=from 0.4 to 2;
b=from 2 to 4;
c=from 3 to 10;
d=from 0.02 to 2;
e=from 0 to 5 and
f=from 0.5 to 10.

14. A process as claimed in any of claims 1 to 3, wherein the active composition has a stoichiometry of the general formula I wherein
$X^1$ = Co;
$X^2$ = at least one element selected from the group consisting of K, Cs and Sr;
$X^3$ = at least one element selected from the group consisting of Zn and P and
$X^4$ = Si.

15. A process as claimed in any of claims 1 to 3, wherein the active composition has a stoichiometry of the general formula II and has three-dimensional regions of the chemical composition $Y^1_{a'}Y^2_{b'}O_{x'}$ which are delimited from their local environment owing to their different composition from their local environment and whose largest diameter is from 1 nm to 100 μm.

16. A process as claimed in any of claims 1 to 3, wherein $Y^1$=Bi.

17. A process as claimed in any of claims 1 to 3, wherein the annular shaped unsupported catalyst precursor body is thermally treated at temperatures which exceed the temperature of 350° C. and do not exceed the temperature of 650° C.

18. A process as claimed in any of claims 1 to 3, wherein the thermal treatment is effected on a belt calciner.

19. A process as claimed in any of claims 1 to 3, wherein said compressing is carried out with a tableting machine or an extrusion reshaping machine.

20. An annular unsupported catalyst having at least one member selected from the group consisting of a curved and uncurved top surface thereof, whose active composition has a stoichiometry of the general formula I

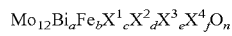 (I)

where
X$^1$=at least one element selected from the group consisting of nickel and cobalt,
X$^2$=at least one element selected from the group consisting of thallium, an alkali metal and an alkaline earth metal,
X$^3$=at least one element selected from the group consisting of zinc, phosphorus, arsenic, boron, antimony, tin, cerium, lead and tungsten,
X$^4$=at least one element selected from the group consisting of silicon, aluminum, titanium and zirconium,
a=from 0.2 to 5,
b=from 0.001 to 5,
c=from 0 to 10,
d=from 0 to 2,
e=from 0 to 8,
f=from 0 to 10 and
n=a number which is determined by the valency and frequency of the elements in I other than oxygen,
or a stoichiometry of the general formula II

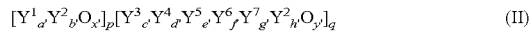 (II)

where
Y$^1$=only bismuth or bismuth and at least one element selected from the group consisting of tellurium, antimony, tin and copper,
Y$^2$=molybdenum or molybdenum and tungsten,
Y$^3$=at least one element selected from the group consisting of an alkali metal, thallium and samarium,
Y$^4$=at least one element selected from the group consisting of an alkaline earth metal, nickel, cobalt, copper, manganese, zinc, tin, cadmium and mercury,
Y$^5$=iron or iron and at least one element selected from the group consisting of vanadium, chromium and cerium,
Y$^6$=at least one element selected from the group consisting of phosphorus, arsenic, boron and antimony,
Y$^7$=at least one element selected from the group consisting of a rare earth metal, titanium, zirconium, niobium, tantalum, rhenium, ruthenium, rhodium, silver, gold, aluminum, gallium, indium, silicon, germanium, lead, thorium and uranium,
a'=from 0.01 to 8,
b'=from 0.1 to 30,
c'=from 0 to 4,
d'=from 0 to 20,
e' is from >0 to 20,
f'=from 0 to 6,
g'=from 0 to 15,
h'=from 8 to 16,
x', y'=numbers which are determined by the valency and frequency of the elements in II other than oxygen and
p, q=numbers whose p/q ratio is from 0.1 to 10,
and whose annular geometry, without taking into account any existing curvature of the top surface, has a length L of from 2 to 11 mm, an external diameter E of from 2 to 11 mm and a wall thickness W of from 0.75 mm to 1.75 mm, and wherein the specific surface area S is from 5 to 20 m$^2$/g and the total pore volume V is from 0.1 to 1 cm$^3$/g, the different pore diameters contributing to V as follows:
pores having a diameter in the range from <0.03 μM: ≦5% by volume;
pores having a diameter in the range from 0.03 to <0.1 μm: ≦25% by volume;
pores having a diameter in the range from >0.1 to <1 μm: ≧70% by volume and pores having a diameter in the range from ≧1 to ≦10 μm: ≦10% by volume, and wherein the annular geometry additionally fulfills the condition L/E=from 0.3 to 0.7.

21. An annular unsupported catalyst as claimed in claim 20 where S=from 5 to 10 m$^2$/g.

22. An annular unsupported catalyst as claimed in claim 20 or 21 where V=from 0.2 to 0.4 cm$^3$/g.

23. An annular unsupported catalyst as claimed in claim 20 or 21, wherein the different pore diameters contribute to V as follows:
pores having a diameter in the range <0.03 μm: ≧0% by volume and ≦5% by volume;
pores having a diameter in the range ≧0.03 to ≦0.1 μm: ≧3 and ≦20% by volume;
pores having a diameter in the range >0.1 to <1 μm: ≧75 and ≦95% by volume and
pores having a diameter in the range ≧1 to ≦10 μm: ≧0 and ≦5% by volume.

24. An annular unsupported catalyst as claimed in claim 20 or 21, wherein the pore diameter d$^{max}$ making the greatest contribution to the total pore volume V is from 0.3 to 0.8 μM.

25. An annular unsupported catalyst as claimed in claim 20 or 21 whose side crushing strength is from 5 to 13 N.

26. An annular unsupported catalyst as claimed in claim 20 or 21 whose ratio of apparent mass density to true mass density is >0.55.

27. An annular unsupported catalyst as claimed in claim 22, wherein the different pore diameters contribute to V as follows:
pores having a diameter in the range <0.03 μm: ≧0% by volume and ≦5% by volume;
pores having a diameter in the range ≧0.03 to ≦0.1 μm: ≧3 and ≦20% by volume;
pores having a diameter in the range >0.1 to <1 μm: ≧75 and ≦95% by volume and pores having a diameter in the range ≧1 to ≦10 μm: ≧0 and ≦5% by volume.

28. An annular unsupported catalyst as claimed in claim 22, wherein the pore diameter d$^{max}$ making the greatest contribution to the total pore volume V is from 0.3 to 0.8 μm.

29. An annular unsupported catalyst as claimed in claim 22 whose side crushing strength is from 5 to 13 N.

30. An annular unsupported catalyst as claimed in claim 22 whose ratio of apparent mass density to true mass density is >0.55.

31. An annular shaped unsupported catalyst precursor body which can be converted by thermal treatment at elevated temperature to an annular unsupported catalyst having at least one member selected from the group consisting of a curved and uncurved top surface thereof, whose active composition has a stoichiometry of the general formula I

 (I)

where
X$^1$=at least one element selected from the group consisting of nickel and cobalt,
X$^2$=at least one element selected from the group consisting of thallium, an alkali metal and an alkaline earth metal,
X$^3$=at least one element selected from the group consisting of zinc, phosphorus, arsenic, boron, antimony, tin, cerium, lead and tungsten,
X$^4$=at least one element selected from the group consisting of silicon, aluminum, titanium and zirconium,
a=from 0.2 to 5,
b=from 0.01 to 5,
c=from 0 to 10,
d=from 0 to 2,
e=from 0 to 8,
f=from 0 to 10 and n = a number which is determined by the valency and frequency of the elements in I other than oxygen, or a stoichiometry of the general formula II

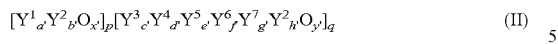
$$[Y^1_{a'}Y^2_{b'}O_{x'}]_p[Y^3_{c'}Y^4_{d'}Y^5_{e'}Y^6_{f'}Y^7_{g'}Y^2_{h'}O_{y'}]_q \quad (II)$$

where $Y^1$ = only bismuth or bismuth and at least one element selected from the group consisting of tellurium, antimony, tin and copper, $Y^2$ = molybdenum or molybdenum and tungsten, $Y^3$ = at least one element selected from the group consisting of an alkali metal, thallium and samarium, $Y^4$ = at least one element selected from the group consisting of an alkaline earth metal, nickel, cobalt, copper, manganese, zinc, tin, cadmium and mercury, $Y^5$ = iron or iron and at least one element selected from the group consisting of vanadium, chromium and cerium, $Y^6$ = at least one element selected from the group consisting of phosphorus, arsenic, boron and antimony, $Y^7$ = at least one element selected from the group consisting of a rare earth metal, titanium, zirconium, niobium, tantalum, rhenium, ruthenium, rhodium, silver, gold, aluminum, gallium, indium, silicon, germanium, lead, thorium and uranium, a' = from 0.01 to 8,
b' = from 0.1 to 30,
c' = from 0 to 4,
d' = from 0 to 20,
e' is from >0 to 20,
f' = from 0 to 6,
g' = from 0 to 15,
h' = from 8 to 16, x', y' = numbers which are determined by the valency and frequency of the elements in II other than oxygen and p, q = numbers whose p/q ratio is from 0.1 to 10, and whose annular geometry, without taking into account any existing curvature of the top surface, has a length L of from 2 to 11 mm, an external diameter E of from 2 to 11 mm and a wall thickness W of from 0.75 mm to 1.75 mm, and which can be obtained by generating a finely divided, shapeable mixture from sources of the elemental constituents of the active composition and, optionally after adding at least one member selected from the group consisting of shaping and reinforcing assistants, compressing this mixture to form an annular shaped unsupported catalyst precursor body whose top surfaces are at least one of curved and uncurved in such a way that its side crushing strength is $\geq 12$ N ands $\leq 23$ N, and wherein the annular geometry additional fulfills the condition L/E=from 0.3 to 0.7.

32. A process for preparing acrolein and/or methacrolein by heterogeneously catalyzed partial gas phase oxidation of propene, isobutene and/or tertbutanol, wherein the catalyst for the gas phase oxidation is an annular unsupported catalyst as claimed in claim 20.

33. A process for preparing acrolein and/or methacrolein by heterogeneously catalyzed partial gas phase oxidation of propene, isobutene and/or tertbutanol, wherein the catalyst for the gas phase oxidation is an annular unsupported catalyst obtained by a process as claimed in claim 1.

* * * * *